(12) United States Patent
Scott

(10) Patent No.: US 8,740,794 B2
(45) Date of Patent: Jun. 3, 2014

(54) METHOD AND APPARATUS FOR ASSESSING OR DETECTING BRAIN INJURY AND NEUROLOGICAL DISORDERS

(75) Inventor: Stephen H. Scott, Kingston (CA)

(73) Assignee: Queens' University at Kingston, Kingston, ON (CA)

( * ) Notice: Subject to any disclaimer, the term of this patent is extended or adjusted under 35 U.S.C. 154(b) by 205 days.

(21) Appl. No.: 13/279,193

(22) Filed: Oct. 21, 2011

(65) Prior Publication Data
US 2012/0101346 A1    Apr. 26, 2012

Related U.S. Application Data

(60) Provisional application No. 61/405,504, filed on Oct. 21, 2010.

(30) Foreign Application Priority Data

Aug. 18, 2011  (CA) ........................... 2749487

(51) Int. Cl.
*A61B 5/00*    (2006.01)
*G06F 19/00*   (2011.01)
*A61B 5/11*    (2006.01)

(52) U.S. Cl.
CPC ............... *G06F 19/34* (2013.01); *A61B 5/4076* (2013.01); *A61B 5/11* (2013.01)
USPC .......................................... 600/301; 600/595

(58) Field of Classification Search
USPC .......................... 600/300–301, 595; 434/236
See application file for complete search history.

(56) References Cited

U.S. PATENT DOCUMENTS

| | | | | |
|---|---|---|---|---|
| 6,561,992 B1 * | 5/2003 | Eberhart et al. | | 600/595 |
| 6,994,670 B2 | 2/2006 | Teicher et al. | | |
| 7,563,234 B2 * | 7/2009 | Cordo | | 601/5 |
| 7,878,811 B2 * | 2/2011 | Earle | | 434/262 |
| 8,475,391 B2 * | 7/2013 | Duffy | | 600/558 |
| 2003/0073885 A1 * | 4/2003 | Theodoracopulos et al. | | 600/300 |
| 2004/0197750 A1 * | 10/2004 | Donaher et al. | | 434/236 |

(Continued)

FOREIGN PATENT DOCUMENTS

CA    2 739 613 A1    4/2010

OTHER PUBLICATIONS

Coderre, A., et al., "Assessment of Upper-Limb Sensorimotor Function of Subacute Stroke Patients Using Visually Guided Reaching," Neurorehabilitation and Neural Repair, vol. 24, Issue 6, 528-541 (2010).

(Continued)

*Primary Examiner* — Bill Thomson
*Assistant Examiner* — Bobby Soriano
(74) *Attorney, Agent, or Firm* — Stephen J. Scribner

(57) ABSTRACT

A method and apparatus is provided for diagnosing, assessing, or detecting brain injury and/or a neurological disorder of a subject. Objects are presented to the subject over a range of locations within the subject's workspace such that the subject can interact with at least some of the presented objects using either the right or left limb, or portion thereof, of a pair of limbs. Position data and/or motion data and/or kinetic data of the left and right limbs or portions thereof with respect to a presented object are obtained, and a data set is acquired for a plurality of presented objects. The acquired data set provides information about brain injury and/or a neurological disorder in the subject.

23 Claims, 15 Drawing Sheets

(56) References Cited

U.S. PATENT DOCUMENTS

| | | | |
|---|---|---|---|
| 2004/0220493 A1 | 11/2004 | Teicher et al. | |
| 2005/0027173 A1* | 2/2005 | Briscoe et al. | 600/300 |
| 2005/0033122 A1* | 2/2005 | Balkin et al. | 600/300 |
| 2005/0187436 A1* | 8/2005 | Doniger et al. | 600/300 |
| 2005/0228240 A1* | 10/2005 | Williams et al. | 600/300 |
| 2005/0283053 A1* | 12/2005 | deCharms | 600/300 |
| 2006/0195018 A1* | 8/2006 | Guillen | 600/300 |
| 2007/0031798 A1* | 2/2007 | Gottfried | 434/236 |
| 2007/0123758 A1* | 5/2007 | Miesel et al. | 600/301 |
| 2007/0141541 A1* | 6/2007 | Chan et al. | 434/236 |
| 2007/0218440 A1* | 9/2007 | Delahunt et al. | 434/236 |
| 2008/0108883 A1* | 5/2008 | Scott et al. | 600/300 |
| 2010/0081889 A1* | 4/2010 | Downs et al. | 600/300 |
| 2010/0178640 A1 | 7/2010 | Yachin | |
| 2010/0179453 A1 | 7/2010 | Schweighofer et al. | |
| 2010/0255449 A1* | 10/2010 | Fadde | 434/236 |
| 2011/0066003 A1* | 3/2011 | Duffy | 600/300 |
| 2011/0091847 A1* | 4/2011 | Carroll et al. | 434/236 |
| 2011/0251468 A1* | 10/2011 | Osorio | 600/300 |
| 2011/0282169 A1* | 11/2011 | Grudic et al. | 600/324 |
| 2011/0306845 A1* | 12/2011 | Osorio | 600/300 |
| 2011/0306846 A1* | 12/2011 | Osorio | 600/301 |

OTHER PUBLICATIONS

Scott, S.H., "Potential of robots as next-generation technology for clinical assessment of neurological disorders and upper-limb therapy," Journal of Rehabilitation Research and Development, vol. 48, No. 4, 335-354 (2011).

Tyryshkin, K., "Bimanual rapid visuomotor task to quantify sensorimotor dysfunction of subjects with stroke," Abstract, Neuroscience 2010, 40th Annual Meeting, Aug. 18, 2010.

International Search Report of the International Searching Authority for PCT/CA2011/001178 filed Oct. 21, 2011.

Written Opinion of the International Searching Authority for PCT/CA2011/001178 filed Oct. 21, 2011.

* cited by examiner

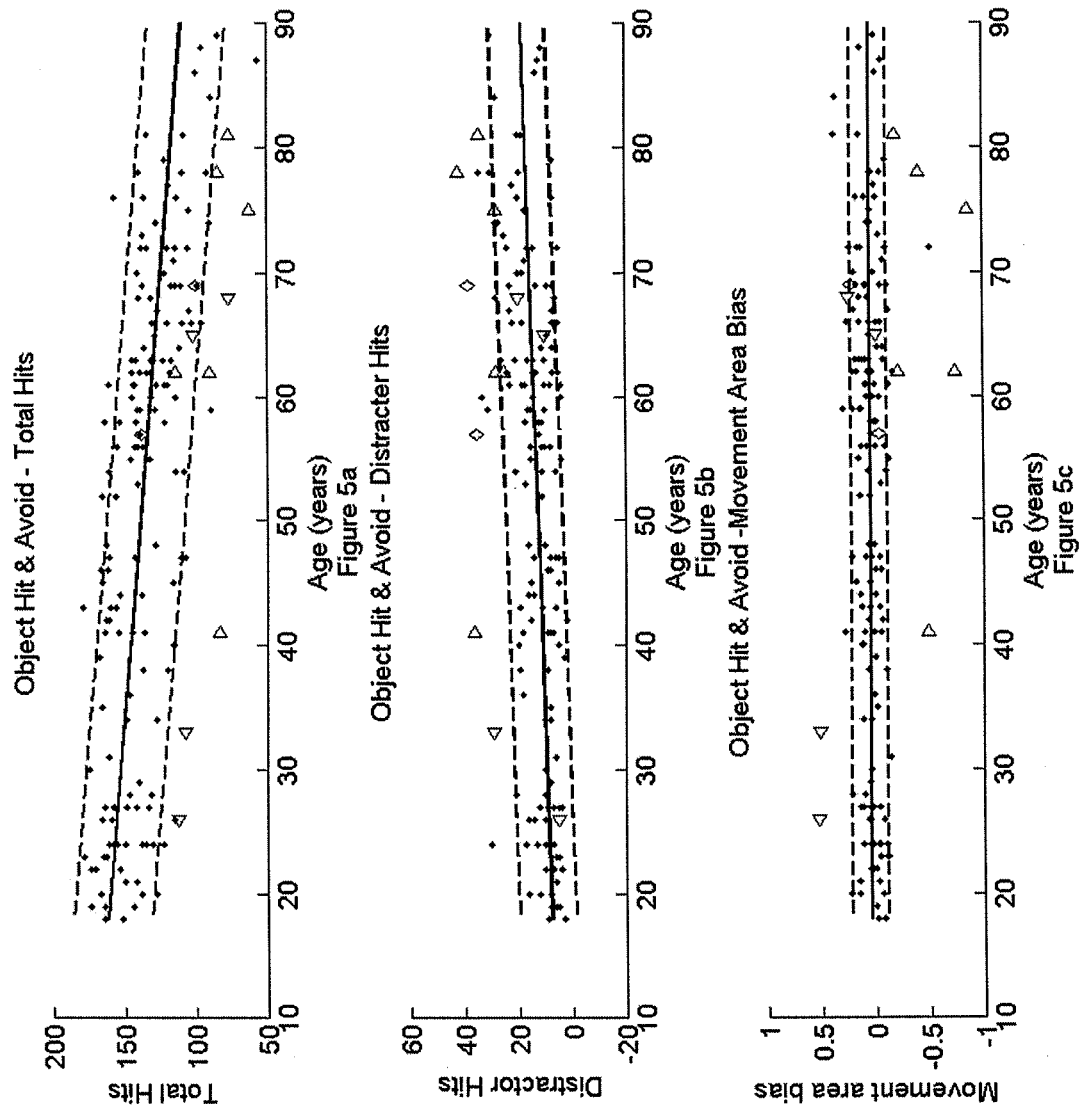

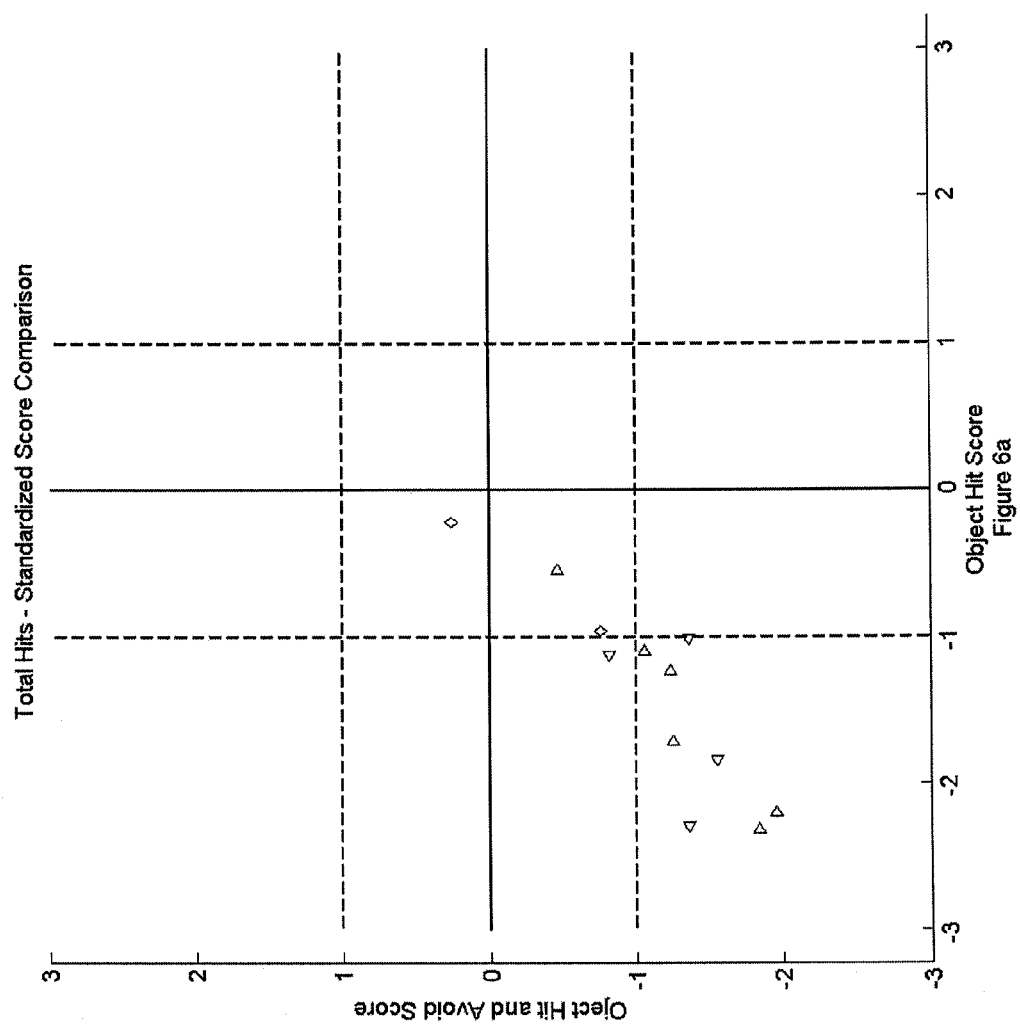

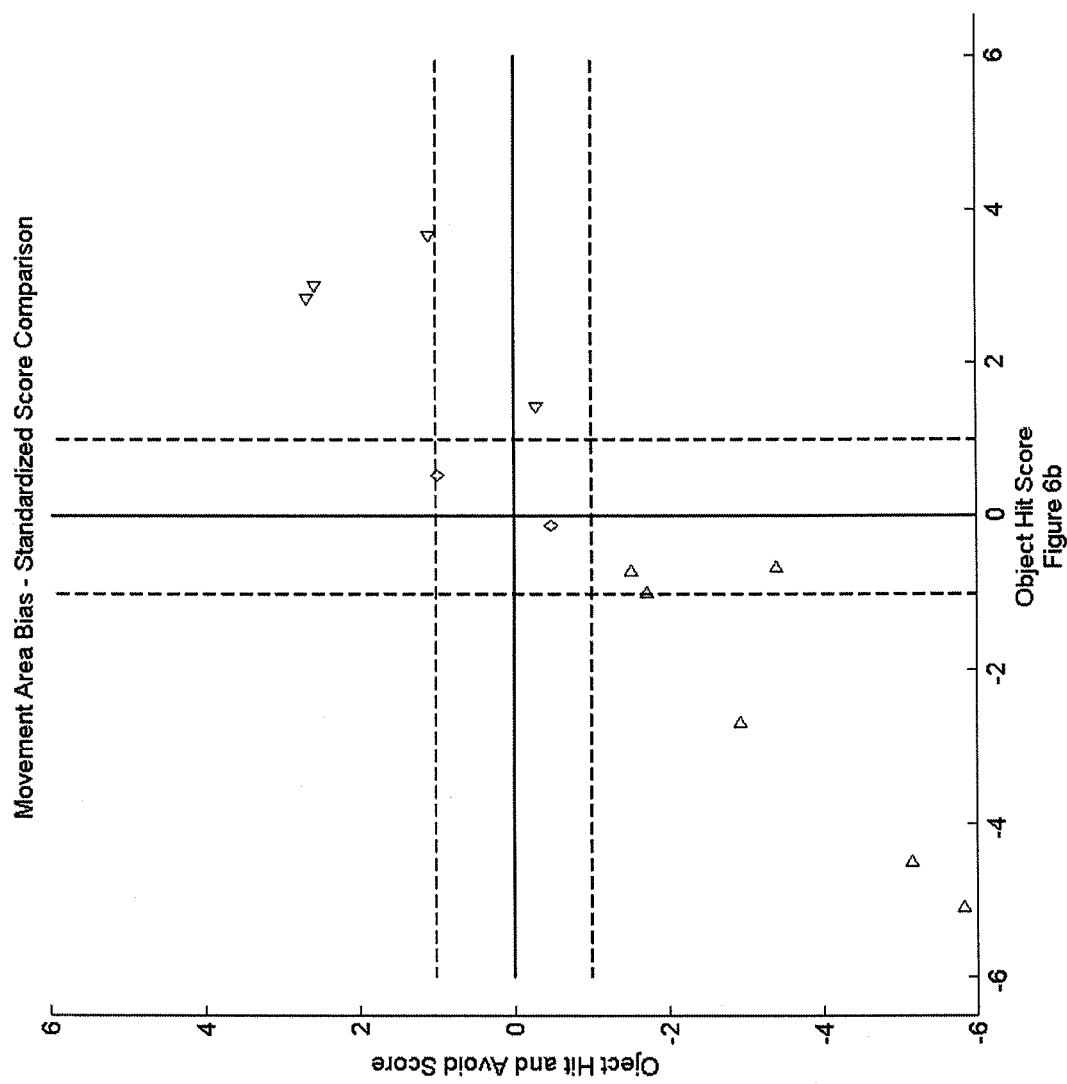

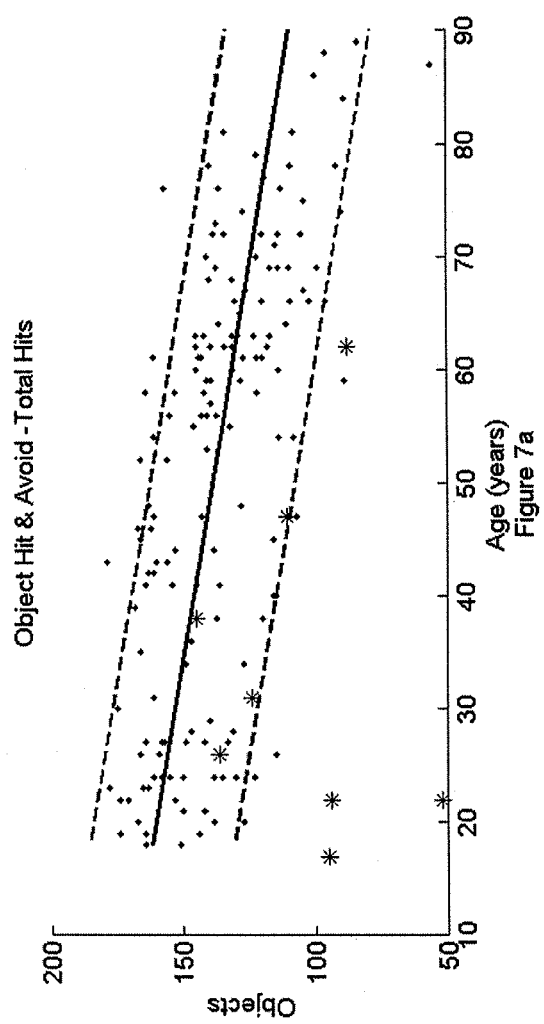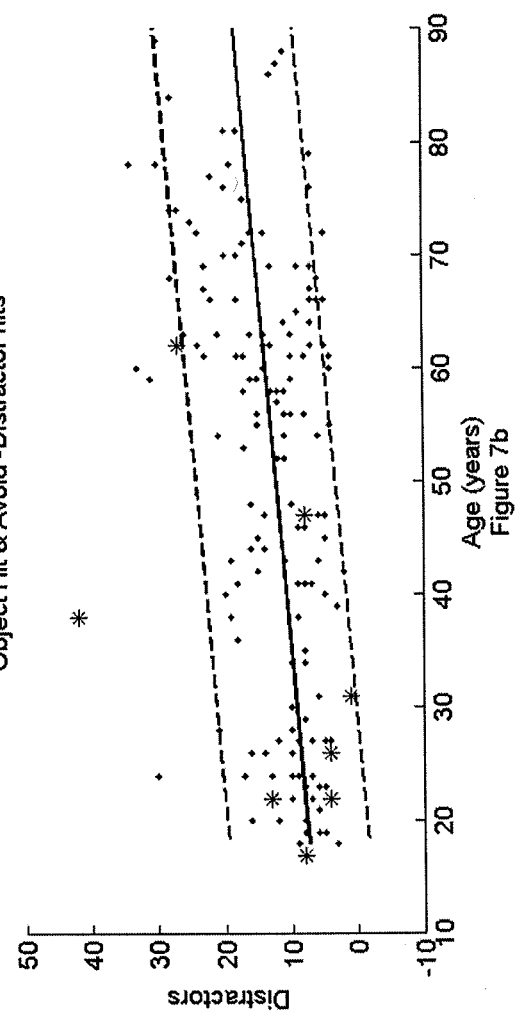

METHOD AND APPARATUS FOR ASSESSING OR DETECTING BRAIN INJURY AND NEUROLOGICAL DISORDERS

RELATED APPLICATIONS

This application claims the benefit of the filing date of U.S. Provisional Application No. 61/405,504, filed on 21 Oct. 2010, the contents of which are incorporated herein by reference in their entirety.

FIELD

This invention provides methods and apparatus for detecting and assessing brain injuries and/or neurological disorders in subjects. In particular, brain injuries and/or neurological disorders that involve impaired sensory, motor, and cognitive processes may be detected and assessed.

BACKGROUND

Movement and interaction within the environment requires a subject to sense the environment using visual, audio, and other sensory processes, as well as sense her/his body position and movement. The sensory, cognitive, and motor processes required are normally performed with speed and accuracy. However, when an individual suffers a brain injury from trauma, stroke, or the like, there can be a broad range of sensory, motor, and/or cognitive functions that are impaired (Teasell et al., 2003), reducing the individual's ability to move and interact within the environment. This leads to a substantive impact on the individuals' ability to perform daily activities.

Clinical assessment plays a crucial role in all facets of patient care, from diagnosing a specific disease or injury, to management and monitoring of therapeutic or rehabilitation strategies to ameliorate dysfunction (Van Dursen and Brent, 1997). Medicine relies on a breadth of technologies and tests to quantify the function of various organ systems that has radically changed the process of diagnosing disease. However, the ability to assess the function of the brain, particularly sensory, motor, and cognitive functions, is surprisingly limited and continues to be based largely on subjective estimates of performance. For example, assessing the ability of a patient to touch their nose and a clinician's finger repeatedly based on a score of 0, 1, or 2. Such subjective rating systems are necessarily coarse to ensure reliability and validity, but such coarseness makes it difficult to detect subtle changes in sensorimotor function. Furthermore, subtle impairments such as small delays in reacting or increases in movement variability cannot be identified easily from visual inspection. Evidence-based reviews of stroke rehabilitation recommend sensorimotor assessments based on ordinal scales. The most reliable of such scales have relatively coarse rating systems, reflecting that it is difficult for even an experienced observer to discriminate small changes in performance using only the naked eye.

A number of pen and paper tasks have been developed to quantify cognitive processes. However, such tasks often do not consider the speed of a subject's ability to complete a task and therefore may be limited in their effectiveness as a tool to assess cognitive processes essential for everyday activites.

Automated processes have been developed such as computer based assessments. For example, CANTAB provides a range of specialized tasks to assess various aspects of cognitive function by having subjects use one of their limbs to contact and interact with a computer screen. Devices such as Dynavision may be used to quantify how subjects respond to stimuli across a large portion of the workspace by recording the reaction time for the subject to hit various targets that are illuminated at random times. Various technologies have also been developed to quantify limb movement, such as robots that can quantify the ability of subjects to make visually guided reaching movements (e.g., KINARM, U.S. Pat. No. 6,155,993 issued 5 Dec. 2000 to Scott).

While such technologies provide a range of information on sensorimotor performance, they lack the ability to assess several key aspects of normal sensorimotor and cognitive function that are crucial for performing daily activities. For example, the decision to reach for an object requires one to decide which limb to use. In many cases, the selection is based on the proximity of the object, the ongoing action of each limb along with general preferences for using one limb over the other for certain tasks (hand preference). Brain injuries are often asymmetric with greater impairments in sensory or motor functions for one side of the body as compared to the other. This may affect how an individual with a brain injury chooses one limb versus the other to perform a task.

A further effect of brain injury may be the subject's inability to respond to or interact with parts of her/his workspace. For example, a subject with a lesion involving the right parietal cortex may have difficulty responding to objects in the left part of the workspace. Traditional pen and paper tasks such as the Behavioural Inattention Test (BIT) may be used to quantify this deficit. However, because a time limit is usually not imposed on subjects performing this task and only a small region of the workspace sampled (i.e., the size of paper used), the test is of limited ability to quantify impairments in this domain.

SUMMARY

One embodiment described herein provides method for diagnosing, assessing, or detecting brain injury and/or a neurological disorder of a subject, comprising: presenting objects to the subject within the subject's workspace such that the subject can interact with the presented objects using either the right or left limb, or portion thereof, of a pair of limbs; using data acquisition apparatus to obtain position data and/or motion data and/or kinetic data of the left and right limbs or portions thereof with respect to a presented object; constructing a data set from the obtained data for a plurality of presented objects; and analyzing the data set and outputting a result that provides information about condition of the brain and/or neurological status in the subject; wherein presenting objects includes presenting objects to the subject within the subject's workspace such that two or more objects are in the subject's workspace simultaneously; or wherein a next object is presented to the subject before the subject can move the right or left limb, or portion thereof, to a selected position after interacting with a previous object.

Also described herein is a method for diagnosing, assessing, and/or detecting brain injury and/or a neurological disorder of a subject, comprising: presenting objects to the subject over a range of locations within the subject's workspace such that the subject can interact with at least some of the presented objects using either the right or left limb, or portion thereof, of a pair of limbs; obtaining position data and/or motion data and/or kinetic data of the left and right limbs or portions thereof with respect to a presented object; acquiring a data set by repeating the obtaining for a plurality of presented objects; wherein the acquired data set provides information about brain injury and/or a neurological disorder in the subject.

Also described herein is a method for diagnosing, assessing, or detecting brain injury and/or a neurological disorder of a subject, comprising: presenting objects to the subject over a range of locations within the subject's workspace such that the subject can interact with at least some of the presented objects using either the right or left limb, or portion thereof, of a pair of limbs; using data acquisition apparatus to obtain position data and/or motion data and/or kinetic data of the left and right limbs or portions thereof with respect to a presented object; acquiring a data set by obtaining position data and/or motion data and/or kinetic data of the left and right limbs or portions thereof for a plurality of presented objects; and analyzing the data set and outputting a result; wherein the result provides information about brain injury and/or a neurological disorder in the subject.

In the methods described herein, the data acquisition apparatus may comprise a mechanical linkage, or wired or wireless sensors adapted to be attached to left and right limbs of a pair of limbs of a subject, and means that detects output signals from the one or more sensors, or one or more cameras, or a combination thereof, to obtain position data and/or motion data and/or kinetic data of the left and right limbs or portions thereof with respect to a presented object.

The methods may comprise determining from the position data and/or motion data and/or kinetic data whether the left limb or right limb was used with respect to a presented object; and repeating the determining for a plurality of presented objects to produce the acquired data set. Determining may include relating location of a presented object within the subject's workspace to the location of the left limb or right limb that was used to interact with the presented object; and repeating the relating for a plurality of presented objects to produce the acquired data set.

The methods may comprise recording one or more autonomic functions of the subject with respect to a presented object; and repeating the recording for a plurality of presented objects; wherein data for the one or more autonomic functions together with the acquired data set provide information about brain injury and/or neurological disorder in the subject. The one or more autonomic functions may be selected from heart rate and blood pressure.

The methods may comprise presenting the objects to the subject using virtual reality or augmented reality; whereby the virtual reality or augmented reality is two-dimensional or three-dimensional.

The methods may comprise using a mechanical linkage to obtain position data and/or motion data and/or kinetic data of the left and right limbs or portions thereof with respect to presented objects; wherein the subject's left and right limbs or portions thereof are in contact with the mechanical linkage. The subject may hold on to the mechanical linkage with the left and right limbs or portions thereof. The left and right limbs or portions thereof may be attached to the mechanical linkage.

The methods may comprise using a motion tracking system to obtain position data and/or motion data and/or kinetic data of the left and right limbs or portions thereof with respect to a presented object.

The methods may comprise determining kinetic trajectory data of a limb with respect to a presented object; wherein kinetic trajectory data provides information about brain injury and/or a neurological disorder in the subject.

The method may comprise determining speed and/or velocity of a limb with respect to a presented object; wherein the speed and/or velocity data provides information about brain injury and/or a neurological disorder in the subject.

The presented objects may include at least one characteristic selected from: (i)
presented objects are stationary; (ii) presented objects are moving; (iii) presented objects are moving at different speeds; (iv) fixed number of presented objects at any given time; (v) variable number of presented objects at any given time; (vi) presented objects have the same characteristics; (vii) presented objects have different characteristics; (viii) duration of visibility of each presented object is the same; (ix) duration of visibility of each presented object is different; wherein data indicating an effect or no effect of a characteristic of a presented objects on the subject's behaviour with respect to a presented object provide information about brain injury and/or a neurological disorder in the subject.

The methods may comprise changing one or more characteristics of the environment in which objects are presented to the subject, including: (i) presenting distracter objects, which the subject is instructed not to interact with; (ii) presenting barriers, real or virtual, that the subject must move around while attempting to interact or not interact with the objects; (iii) presenting workspace-defined force-fields, such as gravity wells; wherein data indicating an effect or no effect of a characteristic of the environment on the subject's behaviour with respect to a presented object provide information about brain injury and/or a neurological disorder in the subject.

The methods may comprise changing one or more characteristics of the subject's interface in the environment, the one or more characteristics selected from: (i) providing body-defined force-fields, as a resistance, force, or bias to the subject's limbs; (ii) modulating spatial and/or temporal alignment of the presented objects relative to the subject's limb movement; (iii) modulating at least one property of a representation of the subject's limbs used to hit or interact with the objects in the environment, wherein the modulated property is selected from width, length, shape, and a combination thereof; and (iv) providing a representation of the subject's limb geometry.

The methods may comprise obtaining gaze position data as the subject interacts with the objects; wherein gaze position data together with the acquired data set provide information about brain injury and/or a neurological disorder in the subject.

In the methods described herein, analyzing may comprise comparing the data set for a subject with control data. A difference between the data set for the subject and the control data may indicate a brain injury and/or neurological disorder in the subject.

Also described herein is a method for obtaining position data and/or motion data and/or kinetic data of the left and right limbs or portions thereof of a subject, comprising: presenting objects to the subject within the subject's workspace such that the subject can interact with the presented objects using either the right or left limb, or portion thereof, of a pair of limbs; using data acquisition apparatus to obtain position data and/or motion data and/or kinetic data of the left and right limbs or portions thereof with respect to a presented object; and constructing a data set from the obtained data for a plurality of presented objects; wherein presenting objects includes presenting objects to the subject within the subject's workspace such that two or more objects are in the subject's workspace simultaneously; or wherein a next object is presented to the subject before the subject can move the right or left limb, or portion thereof, to a selected position after interacting with a previous object.

In another embodiment the method may comprise analyzing the data set and outputting a result that provides information about condition of the brain and/or neurological status in the subject.

In another embodiment the method may further comprise using the result to diagnose, assess, or detect brain injury and/or a neurological disorder in the subject.

Also described herein is a method of diagnosing, assessing, or detecting brain injury and/or a neurological disorder of a subject, comprising: analyzing a data set to determine a brain injury and/or a neurological disorder of a subject; wherein the data set may be obtained by: presenting objects to the subject within the subject's workspace such that the subject can interact with the presented objects using either the right or left limb, or portion thereof, of a pair of limbs; using data acquisition apparatus to obtain position data and/or motion data and/or kinetic data of the left and right limbs or portions thereof with respect to a presented object; constructing the data set from the obtained data for a plurality of presented objects; and analyzing the data set and outputting a result that provides information about condition of the brain and/or neurological status in the subject; wherein presenting objects includes presenting objects to the subject within the subject's workspace such that two or more objects are in the subject's workspace simultaneously; or wherein a next object is presented to the subject before the subject can move the right or left limb, or portion thereof, to a selected position after interacting with a previous object.

In another embodiment the data set may be obtained by: presenting objects to the subject within the subject's workspace such that the subject can interact with the presented objects using either the right or left limb, or portion thereof, of a pair of limbs; presenting one or more distractions to the subject while the subject is interacting with a presented object; using data acquisition apparatus to obtain position data and/or motion data and/or kinetic data of the left and right limbs or portions thereof with respect to a presented object; and constructing the data set by obtaining position data and/or motion data and/or kinetic data of the left and right limbs or portions thereof for a plurality of presented objects.

Also described herein is apparatus for assessing or detecting brain injury and/or a neurological disorder of a subject, comprising: a display device that presents objects to the subject over a range of locations within the subject's visual field such that the subject can interact with a presented object using a left limb or portion thereof, or right limb or portion thereof, of a pair of limbs; a means that obtains position data and/or motion data and/or kinetic data of the left and right limbs or portions thereof with respect to a presented object; wherein the display device displays a representation of the subject's limbs or portions thereof; wherein position data and/or motion data and/or kinetic data corresponding to the subject's left limb and right limb with respect to presented objects provides information about brain injury and/or a neurological disorder in the subject.

According to another embodiment an apparatus for diagnosing, assessing, or detecting brain injury and/or a neurological disorder of a subject comprises: a display device that presents objects to the subject within the subject's workspace such that the subject can interact with the presented objects using either the right or left limb, or portion thereof, of a pair of limbs, wherein the display device displays a representation of the subject's limbs or portions thereof; data acquisition apparatus that obtains position data and/or motion data and/or kinetic data of the left and right limbs or portions thereof with respect to a presented object; and computer readable media that directs a computer to perform one or more of: present the objects on the display device such two or more objects are in the subject's workspace simultaneously; or such that a next object is presented to the subject before the subject can move the right or left limb, or portion thereof, to a selected position after interacting with a previous object; present the representation of the subject's limbs or portions thereof on the display device; input and analyze the position data and/or motion data and/or kinetic data corresponding to the subject's left limb and right limb with respect to the presented objects; and output information about condition of the brain and/or neurological status in the subject.

The means that obtains position data and/or motion data and/or kinetic data of the limbs may comprise a mechanical linkage attached to each limb, or a mechanical linkage grasped by the subject, or one or more sensors attached to each limb, and related hardware for detecting output signals from the one or more sensors.

Also described herein is apparatus for diagnosing, assessing, or detecting brain injury and/or a neurological disorder of a subject, comprising: a display device that presents objects to the subject over a range of locations within the subject's visual field such that the subject can interact with a presented object using a left limb or portion thereof, or right limb or portion thereof, of a pair of limbs, wherein the display device displays a representation of the subject's limbs or portions thereof; data acquisition apparatus that obtains position data and/or motion data and/or kinetic data of the left and right limbs or portions thereof with respect to a presented object; and computer readable media that directs a computer to perform one or more of: present the objects and the representation of the subject's limbs or portions thereof on the display device; input and analyze the position data and/or motion data and/or kinetic data corresponding to the subject's left limb and right limb with respect to the presented objects; and output information about brain injury and/or a neurological disorder in the subject.

The data acquisition apparatus that obtains position data and/or motion data and/or kinetic data of the limbs may comprise a mechanical linkage, or one or more sensors adapted to be attached to each limb, and means that detects output signals from the one or more sensors, or one or more cameras, or a combination thereof.

The apparatus may be configured to carry out one or more of the methods described herein.

BRIEF DESCRIPTION OF THE DRAWINGS

For a better understanding of the invention, and to show more clearly how it may be carried into effect, embodiments will now be described, by way of example, with reference to the accompanying drawings, wherein:

In FIG. 3A, dotted lines are the 5, 50 and 95 quantile regression lines for the female subject group, and dashed lines are the 5, 50 and 95 quantile regression lines for the male subject group. In FIGS. 3C-D, the 5 and 95 quantile regression lines are shown as dotted lines, and the 50 quantile regression line is shown as a thick dashed line.

FIGS. 5A-C are plots showing target object hits (A), distracter object hits (B), and movement area bias (C) as a function of age for the object hit and avoid task. Triangles pointing left represent left-affected stroke subjects, triangles facing right represent right-affected stroke subjects, diamonds represent stroke subjects affected in both hemispheres, small dots represent control subjects. Solid lines are regression fits for the age effects on total hits (i.e., median score corrected for age); dashed lines are at the $5^{th}$ and $95^{th}$ percentiles.

FIGS. 6A-B are plots of normalized comparisons of total hits in an object hitting task versus an object hit and avoid task. Triangles pointing left represent left-affected stroke subjects, triangles facing right represent right-affected stroke subjects, diamonds represent stroke subjects affected in both hemispheres. Median scores were set to zero. Values above the median are normalized by the difference between the median and the $95^{th}$ percentile, whereas values below the median are normalized by the difference between the median and the $5^{th}$ percentile. Solid lines are at the $50^{th}$ percentile; dashed lines are at the $5^{th}$ and $95^{th}$ percentiles.

FIGS. 7A-B are plots of number of hits of target objects (A) and distracter objects (B) in an object hit and avoid task. Large stars denote TBI subjects, whereas small dots denote control subjects. Solid lines are regression fits for age effects on total hits (i.e., median score corrected for age); dashed lines are at the $5^{th}$ and $95^{th}$ percentiles.

DETAILED DESCRIPTION OF EMBODIMENTS

Figure 1:
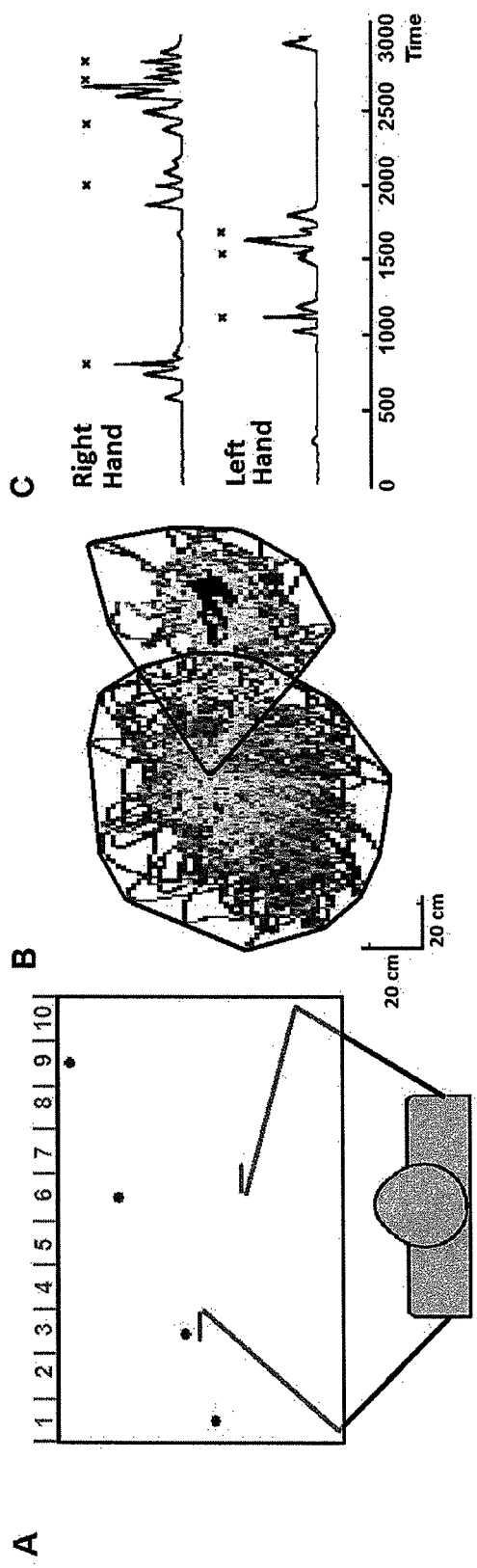
FIG. 1A is a schematic representation of the object hitting task, wherein the objects are balls and virtual paddles are located at the subject's hands.
FIG. 1B is a plot of hand trajectories of a right-affected stroke subject, wherein the black line is a convex polygon that captures the boundaries of the movement trajectories of each hand and captures the area of space used by each hand during the task
FIG. 1C is a sample of average hand speed during the object hitting task, wherein successful ball hits are marked with "x".
FIG. 1D shows performance grids for a control subject (left), a right-side affected stroke subject (middle), and a left-side affected stroke subject with spatial neglect (right), wherein the x-axis represents 10 "invisible" bins from which balls were dropped, and the y-axis corresponds to 30 random blocks, where the top row corresponds to the first random block and the last row corresponds to the last random block. Successful hits made with the right hand are in light grey, hits with the left hand are in dark grey, and misses are shown in white.
FIG. 1E shows the corresponding hits distribution for the subjects of FIG. 1D, wherein the dashed black vertical line represents hand bias and the grey dashed line denotes spatial bias.
FIG. 1F shows the percentage of misses in each bin and the corresponding miss bias for the subjects of FIG. 1D.
Figure 1:
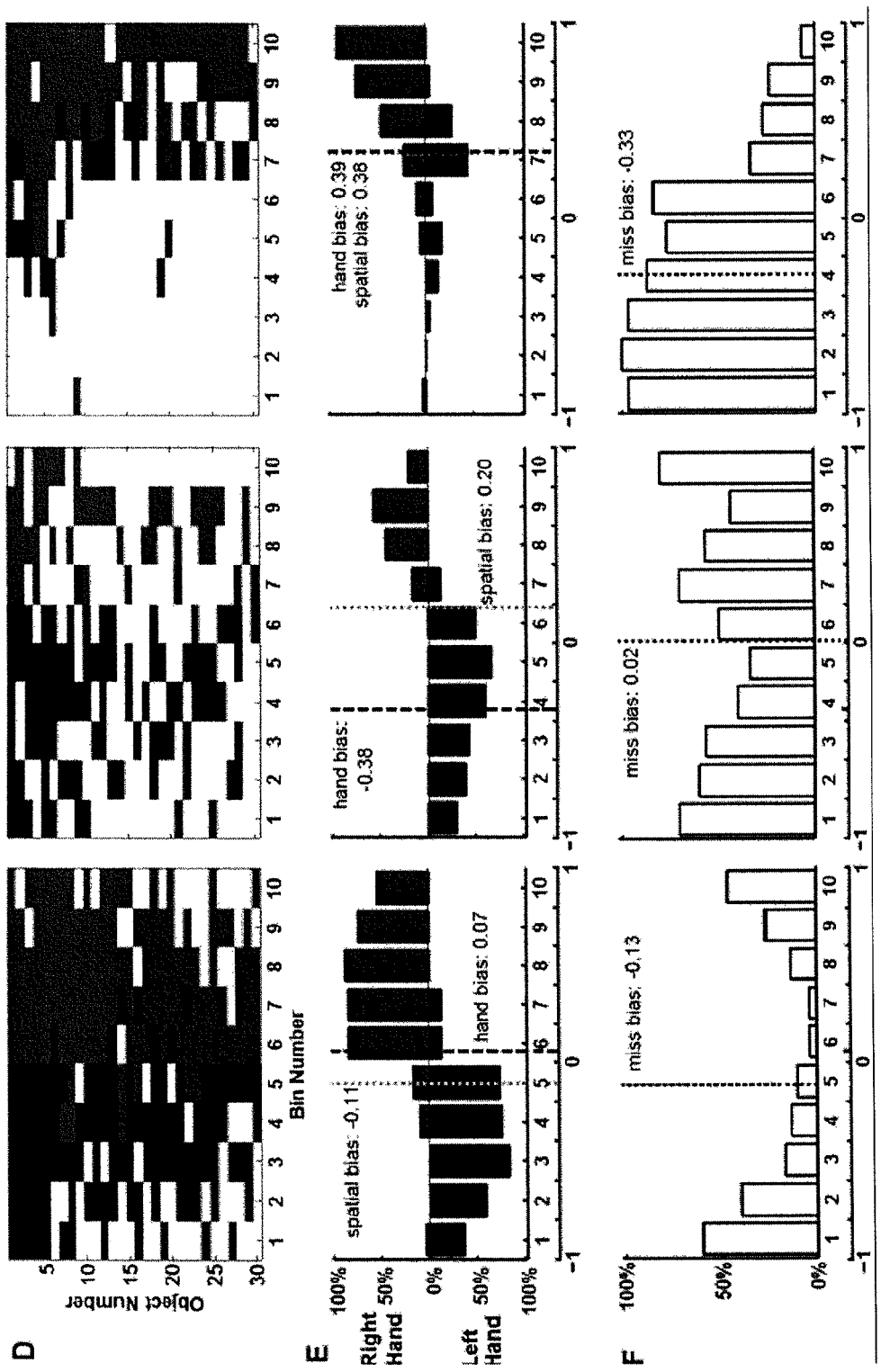

Many daily activities require subjects to move and interact with objects in their environment and involve a broad range of sensory, motor and cognitive processes (i.e., brain functions). Brain injuries and/or neurological disorders may impair one more of these processes, negatively impacting the ability of subjects to perform their daily activities. However, the brain injuries and/or neurological disorders that may be involved cannot be diagnosed, detected and/or assessed satisfactorily with currently-available procedures.

Of particular difficulty is to quantify diseases or injuries that cause modest deficits in performance. Each sensory, motor and cognitive function involves a highly distributed network of cortical and/or subcortical regions of the brain (Kandel, Schwartz and Jessell, 2000). In many cases, these circuits share and overlap for different brain functions, creating a complex interaction across different brain functions during activities of daily living. A vascular incident, concussion, traumatic brain injury, or any other neurological disorder may impair neural processing in only a relatively small portion of the brain or may only impact when two or more brain functions are engaged simultaneously. The distributed nature of neural processing associated with a given function means that impairments in processing in a given brain region can be partially compensated for by processing in neighbouring or other regions within the circuit. Deficits in performance may thus only be observed in more complex situations where these compensating portions of the circuit are also engaged or challenged in other ongoing functions. Thus, deficits in sensory, motor or cognitive function may arise during activities of daily living such as driving a vehicle, when multiple brain faculties must be engaged simultaneously, but may not be easily quantified when assessing the patient using existing clinical assessment tools as these approaches tend to focus on one sensory, motor or cognitive function at a time.

The use of actual or simulated activities of daily living such as driving simulators require multiple sensory, motor, and cognitive functions to perform these tasks but such daily activities cannot separate and disambiguate these myriad functions. As well, certain functions are only rarely required in daily activities but are essential (e.g., avoiding a hazard), limiting the number of test events to evaluate subject performance.

Described herein is an apparatus and a method for obtaining data on the motion, position, and/or kinetics of left and right limbs (e.g., arms) of a subject with respect to real and/or virtual objects in the environment (i.e., workspace; for example, the region of space that the subject can reach using one or both hands). The data correspond to the subject's behaviour with respect to objects in the subject's workspace. The behaviour may include doing nothing with respect to an object, or reacting to and/or interacting with an object. The behaviour may be voluntary or involuntary (e.g., an autonomic function such as heart rate or blood pressure). While the apparatus is useful for obtaining such data from normal, healthy individuals, it is also particularly useful for obtaining such data from individuals with brain injury and/or neurological disorders, as it may aid one or more of diagnosis, treatment, management, and therapy for such individuals.

In the embodiments described herein, position and/or motion and/or kinetics of left and right limbs of a pair of limbs maybe monitored, and the data recorded for analysis. Position and/or motion and/or kinetics of the entire limb (e.g., for the arms: upper arm, lower arm, hand, one or more fingers, and thumb), or any such segment or portion thereof, individually or in combination, may be monitored. Position, motion, kinetics, and rotation of limb joints (e.g., for the arms: shoulder joint, elbow, wrist) may also be monitored and the data recorded. Of course, segments and/or joints of the legs may also be monitored. Such monitoring may be carried out with data acquisition apparatus, which may also be referred to as motion capture apparatus. The data acquisition apparatus may be mechanical or electronic, or a combination thereof, and obtains and outputs position and/or motion and/or kinetics data of the subject's limbs in two-dimensional space or three-dimensional space.

In one embodiment, the data acquisition apparatus may comprise wired or wireless sensors adapted to be attached to left and right limbs of a pair of limbs of a subject, and related hardware for detecting and receiving output signals from the one or more sensors. The sensors are used to monitor limb position and/or motion and/or kinetics in two-dimensional space or three-dimensional space, as the subject interacts with objects that are presented to the subject.

In another embodiment, limb position and/or motion and/or kinetics in two-dimensional space or three-dimensional space may be monitored by using data acquisition apparatus comprising one or more cameras, as the subject interacts with objects that are presented to the subject.

In another embodiment, the data acquisition apparatus may comprise a robotic/mechanical linkage used to monitor position and/or motion and/or kinetics of the limbs. Such linkages maybe grasped by the subject during use, or they may be attached to the limb (e.g., KINARM, U.S. Pat. No. 6,155,993 issued 5 Dec. 2000 to Scott). Robotic/mechanical linkages provide the ability to apply physical loads to the limb of portion thereof, as resistance to or bias against certain motions of the limb, or to simulate contact with virtual objects presented to the subject.

In the embodiments described herein objects presented to the subject may be real objects or virtual objects. Virtual objects may be displayed using, e.g., a display screen and/or projector, or using a virtual reality or augmented reality system.

In the embodiments described herein, subjects interact with presented objects using both limbs, or portions thereof, of a pair of limbs. However, the embodiments may also be applied to a single limb or portion thereof. Further, data may be obtained for right and left limbs, or portions thereof, separately, or simultaneously, using the embodiments described herein.

As used herein, the term "virtual reality" or "VR" refers to an artificial environment into which a subject may completely or partially immerse him/herself, and/or with which the person may interact. The artificial environment may be provided in 2 or 3 dimensions (i.e., 2D or 3D), using any suitable technology. For example, the artificial environment may be computer-generated and adapted (e.g., projected) in a manner that allows the subject to immerse into and/or interact with the environment.

As used herein, the term "augmented reality" or "AR" refers to an artificial environment that includes the features described above for VR, but it also includes aspects of the real world as part of the sensory experience. For example, simultaneous, overlapping views of the real world may be combined with computer-generated images.

In the methods and apparatus described herein, the proprioceptive and visual information obtained retain the natural relationship between the sensory modalities, in that limb afferent feedback of hand position is in register with visual information of its position. This is different from systems that use avatars, such as in computer-based systems (e.g., games such as Wii® and Kinect®), where the subject uses visual feedback of an object or avatar on the screen, but the proprioceptive information still conveys a location of the limb. In this case, the subject must learn how to align and coordinate these two forms of sensory feedback.

The methods and apparatus described herein do not employ hardware, platforms, etc., typically used in applications such as, for example, computer and video gaming and computer-based graphics. For example, such applications may employ hardware such as a mouse or a joystick. Accordingly, diagnosis, assessment, or detection of brain injury and/or a neurological disorder of a subject as described herein avoids any bias that may arise in subjects who are familiar or experienced with such hardware, platforms, etc. The contents of all references, pending patent applications, and published patents cited throughout this application are hereby expressly incorporated by reference.

Embodiments are further described by way of the following non-limiting examples:

EXAMPLE 1

Object Hitting Task

Described herein is an object hitting task, which is an example of a method for assessing or detecting brain injury and neurological disorders. The object hitting task requires a subject to hit objects that move in the subject's environment (i.e., the subject's visual field or workspace) using either limb of a pair of limbs, such as the arms. An embodiment is shown schematically in FIG. 1A, and includes mechanical linkages to obtain position and/or motion and/or kinetics information of the subject's arms, and a VR or AR display device as the subject's workspace. Virtual paddles are displayed as located at the subject's hands and the paddles are moved by moving the arms and/or hands. Objects (e.g., balls) are presented to the subject in the display, and the paddles are used to hit the balls away from the subject. To begin, only one ball is presented at a time and the ball moves relatively slowly towards the subject. With time, the rate at which balls are presented and the speed with which they move through the workspace increases so that after a period of time (e.g., several minutes) balls may move rapidly through the workspace (e.g., in as little as one second), and there may be many balls moving through the workspace at any moment. Most, but not all, of the balls pass through an area of the workspace that is reachable by both hands, such that the subject is forced to choose which hand to use to hit those balls.

The mechanical apparatus used to obtain position and/or motion and/or kinetics information of the arms may be, for example, the KINARM Exoskeleton robot (BKIN Technologies Ltd., Kingston, Ontario) or the KINARM End-Point robot, (BKIN Technologies Ltd., Kingston, Ontario). Both KINARM robots are four-bar linkages that move with two degrees of freedom substantially in the transverse plane. The subject's arms are connected to the KINARM Exoskeleton robot via forearm and upper arm troughs such that the robot's joints are substantially aligned with the subjects' shoulder and elbow joints. In contrast, the subject interacts with the KINARM End-Point robot by grasping a handle, such that the robot's handle is substantially aligned with the subject's hand. Both systems can provide force/haptic feedback to simulate ball contact and incorporate two-dimensional virtual/augmented reality systems for visually presenting the balls to the subject.

In one embodiment the balls move within the workspace in the transverse plane and their locations in space are varied so that some balls move to the left of the subject's midline and other balls move to the right of the subject's midline, although some balls may also be located on the subject's midline. The number of balls to the left may be equal to the number of balls to the right of the subject. This embodiment requires a subject to identify the location and speed of each ball moving in the workspace, select one of the two arms with which to hit the object (using the virtual paddles), and then execute a motor action to hit the ball. Data collected relate to which limb (left or right) is used for each ball, and other parameters such as mean hand speed and ball contact force.

An integral part of this task is the selection of the limb used to hit the object for those objects that can be reached by both limbs. In control subjects, there is substantially equal use of the two limbs and the point of transition between using the left and right limbs tends to be near the middle of the workspace (although there may be a small bias to using the right hand more and shifting the transition to the left side in right-handed individuals, and vice-versa in left-handed individuals). Other parameters of the task, such as mean hand speed and ball contact force, are characterized by a high degree of symmetry for control subjects.

However, in subjects with disorders or diseases such as stroke there can be differences in the motor skills of the two limbs. The task quantifies these differences by recording data calculating a range of parameters related to how the hand/limb hits the objects and the pattern of movement of each limb within the workspace.

A unique feature of the task is that not only are asymmetries in use of the two limbs quantified, but also how and where the two limbs are used in the workspace. For many stroke subjects, there is a natural trade-off as to how often a limb is used to hit an object and the spatial transition point where one limb tends to be used more than the other. Subjects that predominantly use their left hand to hit objects tend to have a transition point located on the right side of the workspace (See FIG. 2C).

However, some stroke subjects do not show this trade-off and instead show preferential use of one limb, but no shift in the spatial transition point, or a shift in the same direction as the hand preference. FIG. 1D (right panel) shows an example of one such subject that used the right hand more than the left, but the spatial bias was located on the right side of the workspace. This subject also displayed a greater number of misses to the left versus the right. Importantly, this subject was identified as having spatial neglect using the BIT test (BIT score 105). Several other subjects with clinically defined spatial neglect also showed this pattern of behaviour (Solid triangles in FIG. 2C). These results demonstrate how the object hitting task described herein can identify different patterns of behaviour resulting from brain injury.

Variations of the Task

In one embodiment the object hitting task is a basic task that requires both limbs to be engaged in ongoing motor actions and involves the subject planning and selecting for impending motor actions with each limb, and thus provides key information on these processes. However, this basic task creates a foundation for quantifying other aspects of brain function, which in other embodiments may include strategically manipulating one or more features of the task.

In such embodiments, variations in the object hitting task permit more detailed and specific examination of different aspects of a subject's performance. For example, the task may be performed with smaller paddles to enhance the difficulty of hitting the objects, to emphasize the importance of movement accuracy to successfully perform the task. Such additional challenges in the task stress associated circuits in the brain involved in that process, and/or impact upon other ongoing processes due to overlap in neural processing involved in these brain functions. Thus, a change in performance across variations of the task provides information on brain processes that are specifically challenged by the task variation, but also on brain processes that are shared across two or more tasks.

Another variation of the task is to include distracters, that is, objects in the workspace that are not meant to be contacted by the subject. Distracters may have different characteristics than objects meant to be contacted by the subject. For example, a distracter may be a different colour and/or shape, or move in a different trajectory or speed within the workspace, than an object meant to be contacted by the subject. For example, a subject could be instructed to hit circular objects, and not to hit square objects. Such distracters increase the cognitive requirements of the task by requiring subjects to identify the properties of each object before deciding whether to hit the object or not. A further variation may be to have a subject hit circular objects but specifically avoid hitting any of the distracters in the workspace. In such a hit and avoid task the use of distracters demands greater attention of the subject and requires inhibitory processes in the brain so as to avoid contact with the distracters. In another embodiment a distracter may include presenting audio (i.e., sound) to the subject, which may or may not have an association with either the subject's behaviour and/or a presented object.

Another variation may include adding barriers to the workspace, such that the subject must navigate around the barriers to interact with the objects.

Another variation may include adding one or more 'gravity' wells or other force-fields in various locations within the workspace. Gravity wells or other force-fields may be of uniform strength or they may vary in strength (of force) from one to another. Such force-fields are defined with respect to the subject's workspace.

Another variation may include adding a delay to the visual feedback (e.g., a display screen) of where the limbs are in the workspace.

Another variation may include changing the physical mapping between the limbs and the workspace (e.g., visual feedback may be provided on a screen in front of the subject, rather than as a VR setup).

Another variation may include making all objects stationary.

Another variation may have objects appear for a brief period of time.

Another variation may have only one object presented at time and appear rapidly after the previous object has disappeared.

Another variation may include making all objects visible immediately.

Another variation may require more complex cognitive decisions such as hitting an object after a different object has been displayed. For example, the task might require the subject to hit any object that appears following the presentation of a circular object.

Another variation may include modifying one or more properties of the subject's interface (i.e., properties of the display and/or mechanical and/or physical attributes of the subject's environment) to make it asymmetric with regard to the difficulty required to hit objects. For example, the paddles used to hit objects may be of different sizes for each limb, or include a representation of the limb's geometry (e.g., upper arm, forearm, and/or hand).

Another variation may include adding a limb-based force-field or "body-defined" force field, such as viscosity (e.g., to resist limb movement; to make the limb it feel like it is moving through molasses) or by adding an inertial load (e.g., to make the limb or portion thereof, such as the hand, feel like it is heavier). Such force-fields are defined with respect to the subject (e.g., limb velocity).

Another variation may include making the midline of the workspace substantially aligned with the midline of the subject.

Another variation may include gaze-tracking of the subject during the task including any variation thereof, such as the variations described above. Gaze direction may then be compared to the subject's movements, to determine, for example, if an object was not hit, did the subject look at the object or not.

Another variation may include coupling (e.g. mechanically, visually or through other means) two limbs together so that the limbs must be used together in a coordinated fashion to hit an object. For example, coupling may require the subject to grip an effector with both hands simultaneously, such that moving the effector to hit an object requires coordinated movement of both limbs.

Another variation may include asking the subject to stand while performing the task.

Another variation may include having the subject perform the task with only one limb.

Another variation may include recording data about the subject's posture while performing the task (e.g., using a force-plate).

Another variation may include using a motion tracking system to track position and/or motion and/or kinetics of the limbs (e.g., using passive or active markers, or a markerless system).

Another variation may include using force feedback to control the position and/or motion and/or kinetics of one or more properties of the subject's interface.

Other variations may include other means to engage other regions of the subject's brain while performing this task.

For a given variation of the task (as described above), differences in target characteristics may be introduced to avoid learning effects; however, providing those differences instances with a substantially equal level of difficulty ensures that the results are meaningful and/or comparable. For example, when introducing one or more distracter objects in the workspace, the distracter shape(s) may be chosen to be substantially different from the target shapes. Each such variation in the task provides further information on its own, whereas comparisons of performance across task variations provides additional information on how each component of the task directly impacts behavioural performance.

In some prior tasks, objects are presented to subjects in a way that allows the subject to recover from a presentation of an object and/or prepare for presentation of a next object. For example, given sufficient time, a subject may prepare for presentation of a next object in one or more ways, such as mentally (e.g., by concentrating, anticipating the next object, etc.), and/or physically (e.g., by moving one or both limbs or portions thereof to a selected position (i.e., a new, substantially different position, including, e.g., a ready position, or a defined starting position)). Insofar as this may be a drawback for some assessments, embodiments of certain tasks described herein decrease or eliminate the duration of time a subject has to recover from presentation of an object, and/or decrease or eliminate duration of time a subject has to prepare for the presentation of a next object. Such embodiments can provide substantially more information about a subject's sensory, motor, and cognitive brain functions, compared to tasks that permit recovery and/or preparation time in respect of presented objects, and may enhance diagnosis, assessment, and/or detection of brain injury and/or neurological disorders.

As used herein, the term "distraction" includes any stimulus presented to a subject that may challenge or interfere with the subject's ability to interact with an object. For example, a distraction may include any of the distracters discussed herein, or any of the variations of the tasks discussed herein that provide such a challenge to the subject.

EXAMPLE 2

Evaluation of Stroke Subjects

Participants

Stroke subjects were recruited from the stroke rehabilitation wards at Providence Care, Saint Mary's of the Lake Hospital site in Kingston, Ontario, and from Foothills Hospital in Calgary, Alberta. The stroke patients had a single stroke that resulted in cortical, subcortical, cortical-subcortical, brainstem, cerebellar, or mixed lesions. The subjects were broadly categorized into right affected (RA) or left affected (LA) based on the most affected side of the body. Age-matched control subjects (people with no neurological disorders) were recruited from the community. Participants were excluded if they could not understand the task instructions. Each subject underwent a typical stroke assessment and one robotic session (described below), where several tasks were performed for each arm, including the object hitting task.

Clinical Evaluation

The procedure and the documented clinical parameters that were used in this study have previously been described [Dukelow et al., 2010, Coderre et al., 2010]. The clinical evaluations were performed by the study physician or physiotherapist. The clinical parameters included the handedness score, Behavioural Inattention Test (BIT), Mini-Mental Status Exam (MMSE), Montreal Cognitive Assessment (MoCA), Functional Independence Measure (FIM), and Chedoke-McMaster Stroke Assessment Scale for hand and arm (CMSAh and CMSAa). Previous reports showed that control subjects obtained perfect scores with each limb on both the arm and hand portion of the CMSA (CMSAa and CMSAh) [Coderre et al., 2010], therefore, in this study the CMSA clinical assessment was not performed for the control group.

Robotic Assessment

Performance of subjects during the task was monitored using the bimanual KINARM exoskeleton robot, (BKIN Technologies Ltd., Kingston, Ontario). The details of the KINARM robot setup were previously described [Dukelow et al., 2010, Coderre et al., 2010]. Briefly, a subject was seated in a wheel-chair base while their arm segments (arms, forearms and hands) were placed in plastic arm troughs attached to an adjustable four-bar linkage of the KINARM. The experimenter adjusted the linkage and the troughs for each subject insuring comfortable and correct position of the subject during the experiment. The KINARM allowed free horizontal hand movements while providing full gravitational support for subject's arms. The task's visual targets were projected via mirrors onto a virtual horizontal workspace positioned in the same plane as subject's arms. The virtual environment was achieved by occluding direct vision of a participant's arms and projecting hand position on the screen as two green paddles, and the objects ("hit targets") were presented as red balls.

Experimental Task

In the object hitting task subjects were instructed to use their right and left hands, represented as green paddles, to hit red balls that were moving towards them on the screen (see FIG. 1A). The objective of the task was to hit as many balls as possible. The balls appeared on the screen from 10 different bins, whose locations were not shown. Each task consisted of continuously running 30 random sets. Ten balls were used in each set, and each ball appeared from one of the 10 "invisible" bins in random order. Consequently, the game consisted of a total of 300 balls falling continuously on the screen. The number of balls that appear on the screen and the speed of the ball movement increased as the task progressed. Force feedback was generated by the KINARM robot each time a paddle hit a ball. During the task, positions of the hands and active balls were recorded with a sampling frequency of 200 Hz (one sample every 0.005 seconds).

Data Analysis

Data analyses were performed using MATLAB (Mathwork, Inc., Massachusetts, USA). First, the control data was analyzed and nine parameters were developed to quantify task performance, hand usage, and motion. Then a non-least-squares linear regression was performed to identify age-dependent parameters and to eliminate trend in the data. The resulting values for the nine parameters for the control data were separated using five quantiles (5%, 25%, 50%, 75%, 95%). Stroke patients that fell out of the 5-95% inter-quantile range of the control group were considered as impaired in terms of their performance.

Parameters

Ten parameters were developed to characterize performance and to quantify task performance, hand usage, and motion.

Number of misses: captures the overall performance of a subject. This parameter simply sums up all the missed balls during the task for each bin. A ball hit is valid only when a subject hits the ball with a paddle and the ball leaves the display area either at the top or on one of the sides. Alternatively, overall performance may be quantified by object or target hits, or based on a percentage of misses or hits.

Miss bias: quantifies any bias of misses towards one side or another. It is computed by counting the number of misses for each of the ten bins and then calculating the weighted mean of the resulting distribution over the ten bins.

Hand bias of hits: captures participant's preference and ability for using one hand over the other for successfully hitting the balls (hand dominance). It is the normalized difference between the total number of hits with right (RH) and left (LH) hands: (RH hits–LH hits)/(RH hits+LH hits).

Hand overlap or hand selection overlap: captures how effective participants are at using both hands and how often they overlap their hands (i.e., hit the balls with the right hand in the left area of the screen, and vice versa). The parameter is computed by calculating the sum of absolute differences between the right and left hand hits in bins where both hands made hits. An alternative method is by counting the number of times that two successful hits of balls from a given bin were hit by different hands (i.e., ball hit by left hand and the next ball from that bin was hit by the right hand, or vice versa). The final count is then divided by the total number of hits.

Spatial bias of hits or hand transition: shows where the subject's preference for using one hand over the other switches in the workspace. To compute this bias, first, the integral is taken of differences between left and right hand hits for each bin. Then the resulting data are interpolated using a cubic spline, and the spatial bias of hits is the peak of the resulting curve. Alternatively, this parameter may be computed by taking the mean of two values: the right hand and the left hand weighted means of hit distributions. The weighted mean of hit distributions for each hand is calculated independently for each hand using a subset of bins, including only those where both hands made hits (overlapping bins) plus one additional bin on each side of the overlap bins. In the case where no overlap occurs, the subset of bins used includes the right-most bin in which hits were made by the left hand and the left-most bin where hits were made with the right hand.

Hand area or hand movement area: captures the area of space used by each hand during the task. It is computed as the area of the convex hull, which is a convex polygon that captures the boundaries of the movement trajectories of each hand. The hand area parameter is computed for each hand separately resulting in two parameters.

Hand bias area or movement area bias: shows the bias in using one hand over the other with respect to the total area of the hand movement. It is computed by subtracting the hand area of the left hand from the hand area of the right hand and then normalizing by the total area of both hands (RH–LH)/(RH+LH).

Mean hand speed: is computed as the mean of the hand speed at each time step (every 0.005s) of the experiment. The parameter is computed for each hand separately resulting in two measures.

Hand bias speed: quantifies the bias in using one hand over the other with respect to the average hand speed. It is computed by subtracting the mean hand speed of the left hand from the mean hand speed of the right hand and then normalizing by the sum of the mean hand speeds of each hand RH–LH)/(RH+LH).

Median error (ball %): quantifies the point in the task where the subject missed half of the balls. It is computed by finding the ball (or time index) when half of the misses were made by the subject and then compute the percentage of total possible misses. Large scores mean that the subject performed relatively well when the task was easy and failed predominantly only at the end of the task when the task difficulty was greatest.

Results

Participant Pool

Data were collected from 35 stroke subjects (18 left- and 17 right-affected) and 39 age-matched control subjects. Table 1 shows the summary of collected demographic and clinical data for all subjects. The majority of the subjects were right-hand dominant (n=66 out of 74), and there was no difference in the distributions of age across the three participant groups (Kolmogorov-Smirnov (KS), P>0.05). The majority of the stroke patients had ischemic stroke (69%) and predominantly in the cortical area of the brain (49%). Five out of 35 stroke subjects had spatial neglect (BIT score<130).

Clinical Measures

The clinical measures for the stroke participants are presented in Table 1. There were no differences between left- and right-affected participants on the FIM (cognitive, motor and total), MMSE, or MoCA scores (Wilcoxon 2-sided rank sum test, P>0.05). However, there was a difference between left- and right-affected participants on the BIT (Wilcoxon 2-sided rank sum test, P<0.01) score: left-affected had significantly lower scores. Based on CMSAa and CMSAh scores, the participants obtained worse scores with their affected arm as compared to their unaffected arm (Wilcoxon 2-sided signed rank test, P<0.01).

Robotic Assessment

Individual Subject Exemplars

The performance plots and results for some of the parameters are shown for exemplar data in FIGS. 1D-F. The exemplar data consist of a control subject (left), a right-affected stroke subject (middle) and a left-side affected stroke subject with spatial neglect (right).

The performance grid of the control subject illustrates a pattern of a normal performance. It shows small number of misses, mostly on the far left or far right sides of the screen and mostly towards the end of the task, when ball speed is high. FIG. 1E shows the corresponding hits distribution for the control subject and two parameters: hand bias (dashed line) and spatial bias (dotted line). The control subject has a hand bias and spatial bias near, indicating symmetric use of the hands. The miss bias for the control subject (FIG. 1F) is slightly shifted to the left, indicating that more misses were observed on the left side of the field, which may be due to the fact that this control subject is right-hand dominant.

The first stroke subject (in the middle) has different spatial and hand bias. The subject clearly prefers using the left hand over the right stroke-affected hand. The negative hand bias indicates that the subject hit more balls with the left hand, and the positive spatial bias indicates that the subject covered more space of the screen with the left hand than with the right hand. The miss bias for this stroke subject is near the center and shows that balls were missed near equally on both sides of the screen.

The second stroke subject (on the right) shows equal spatial and hand bias, however they are shifted to the right and the screen area on the left is almost completely untouched. This supports the clinical assessment results, which indicates that this stroke participant has spatial neglect (BIT score=129). This negative miss bias indicates that most of the balls were missed on the left side of the screen, such that in bins 1, 2 and 3 the balls were almost completely missed.

Age Effect

A regression analysis, using non-least-squares linear regression was performed to identify which parameter values are affected by the age of the subject. The results indicated that only the "number of misses" parameter showed a slope at the 1% level of significance and, therefore, is affected by the age of a subject. Consequently, in further analysis the data of the "number of misses" parameter were de-trended.

Performances of Control and Stroke Groups

Table 2 shows the percentage of stroke participants that were identified as different from controls based on their affected arms. The parameters that identified the largest number of stroke participants as abnormal were the following: hand overlap (94% of left- and 41% of right-affected), hand bias area (89% of left- and 41% of right-affected), hand bias of hits and hand bias speed (83% of left- and 59% of right-affected). The parameters that identified the least number of stroke participants as abnormal were the following: number of misses (12% of left- and 28% of right-affected), hand area right hand (24% of left- and 11% of right-affected), and miss bias (35% of left- and 11% of right-affected).

FIGS. 2A-D highlight some of the range of performance across subject groups.

Figure 2A:
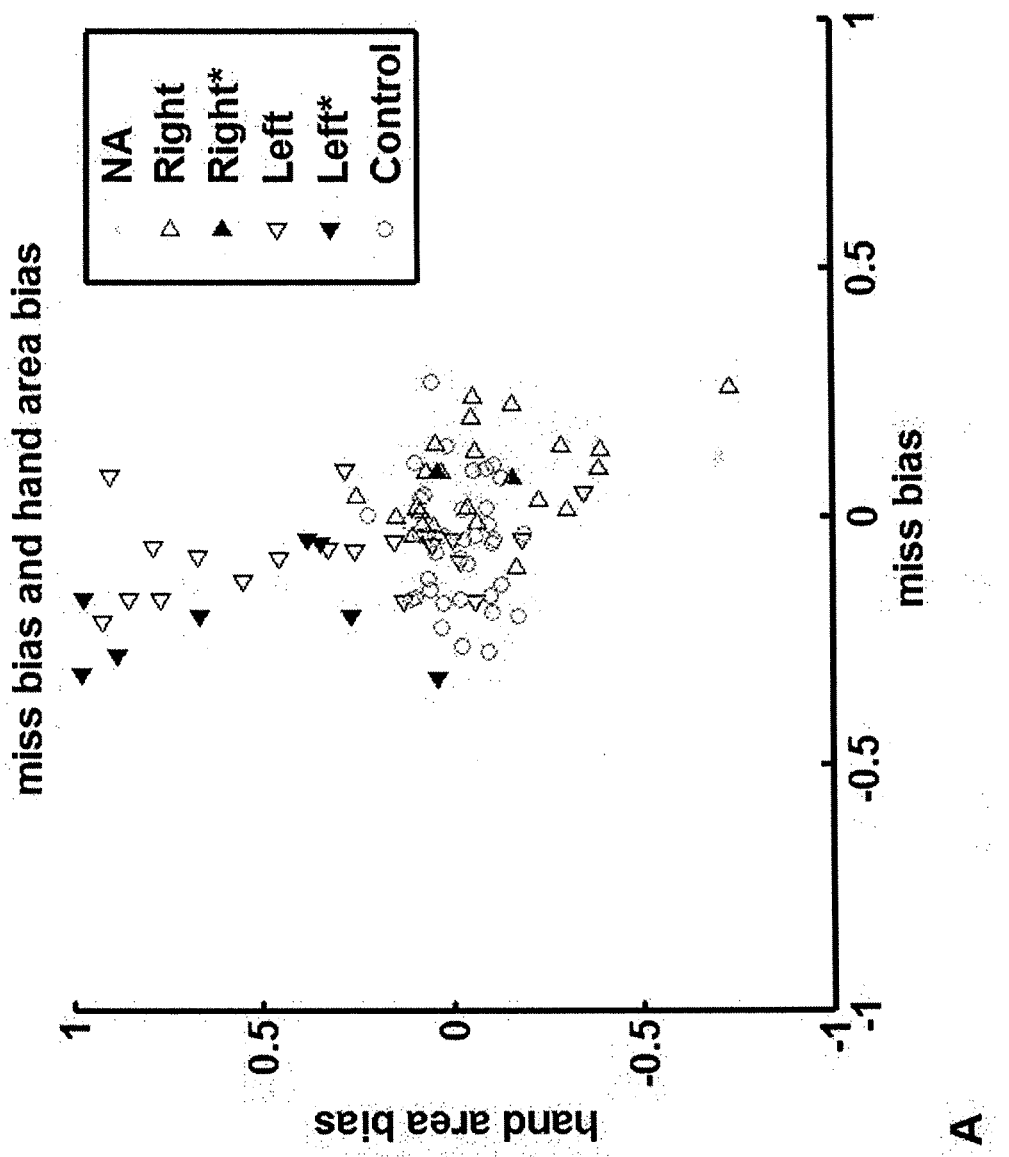
FIG. 2A is a plot showing miss bias with respect to hand bias area for subjects performing an object hitting task as described herein.

FIG. 2A shows miss bias with respect to hand area bias. The control subjects tend to have hand area bias close to zero; whereas majority of right-affected stroke participants showed negative bias and left-affected subjects showed positive bias reflecting the fact these subjects had larger hand areas for their non-affected hand than for their affected hand. Similarly, the miss bias, although as not effectively, separates left-affected and right affected stroke participants into two groups, such that left-affected subjects are to the left of the screen (negative bias, more misses on the left side) and right-affected subjects tend to be on the right side of the screen (positive bias, more misses on the right side).

Figure 2B:
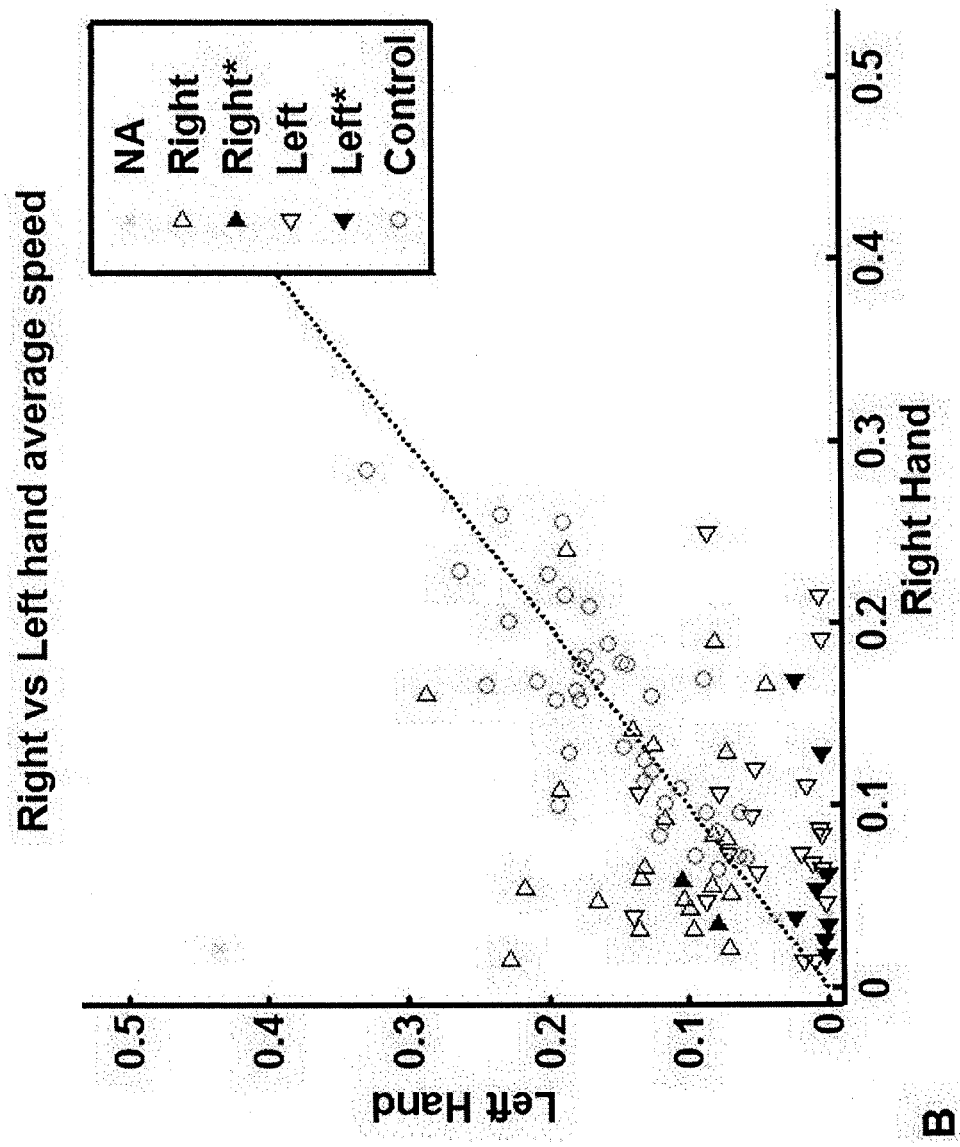
FIG. 2B is a plot showing average speed of the left and right hands of subjects performing an object hitting task as described herein.

FIG. 2B displays the average speed for the left and right hands. There was a broad range of speeds utilized by control subjects, ranging from 0.06 m/sec to 0.27 m/sec. However, there was a strong correlation between speed of two hands, indicating that control subjects moved both arms either slowly or both arms quickly. The majority of the stroke participants, on the other hand, showed slower speed for their affected arm than for the non-affected arm. Furthermore, there were often greater differences in the speed of the two hands.

Figure 2C:
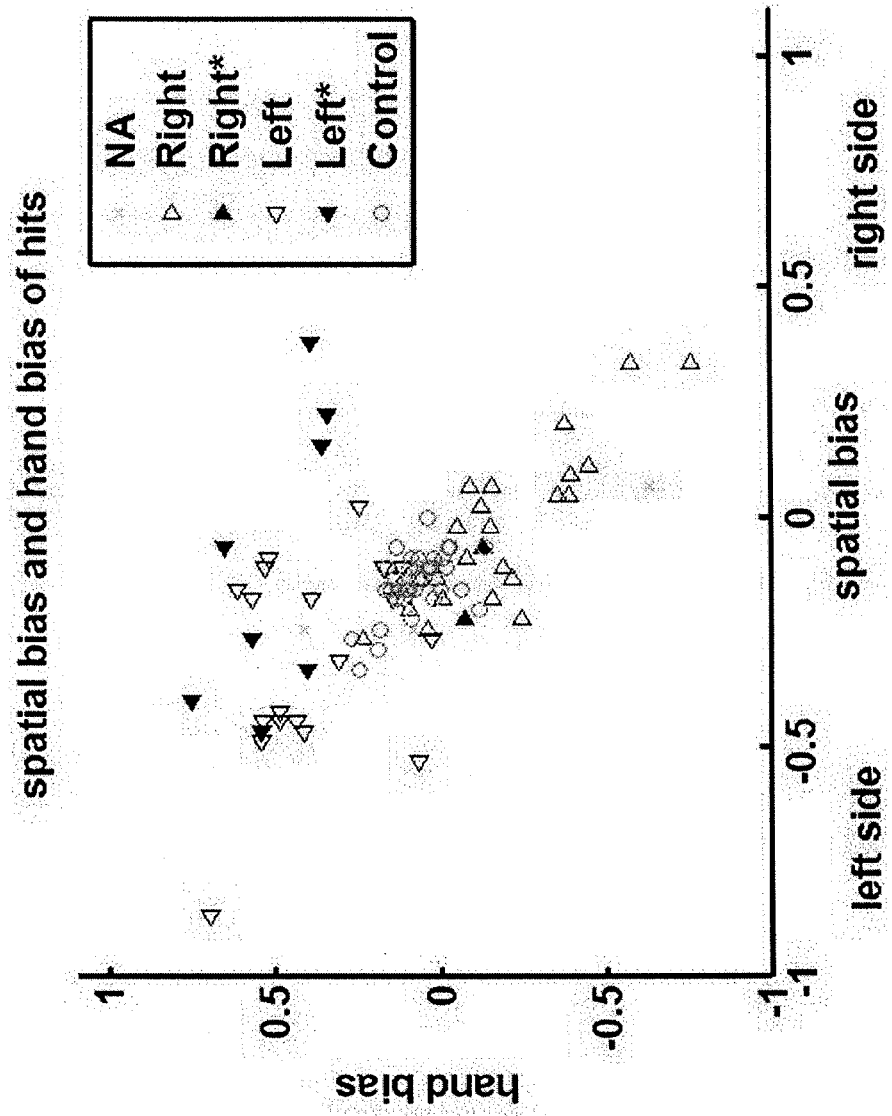
FIG. 2C is a plot showing spatial bias versus hand bias of hits for subjects performing an object hitting task as described herein.

FIG. 2C shows results of the spatial bias versus hand bias of hits. Similar to other biases, control subjects have spatial and hand biases of hits close to zero. Left-affected stroke participants showed negative spatial bias because they made more hits and covered more space with their non-affected, right hand. Similarly, majority of the right-affected stroke participants made more hits and covered more space with their non-affected left hand which resulted in positive spatial bias. The hand bias of hits was negative for the left-affected stroke participants and positive for the right-affected stroke participants, since subjects tend to make more hits with their non-affected hand. Consequently, results of typical stroke patients and control participants form a line, such that controls are in the center, right-affected participants are on the right side and left-affected participants are on the left side of the line. However, stroke patients with specific deficits fall out of this pattern. For example, the exemplar participant from FIG. 1D-F (middle) has positive hand and spatial bias of hits and fell out of the "line pattern" (FIG. 2C, the right most solid triangle).

Figure 2D:
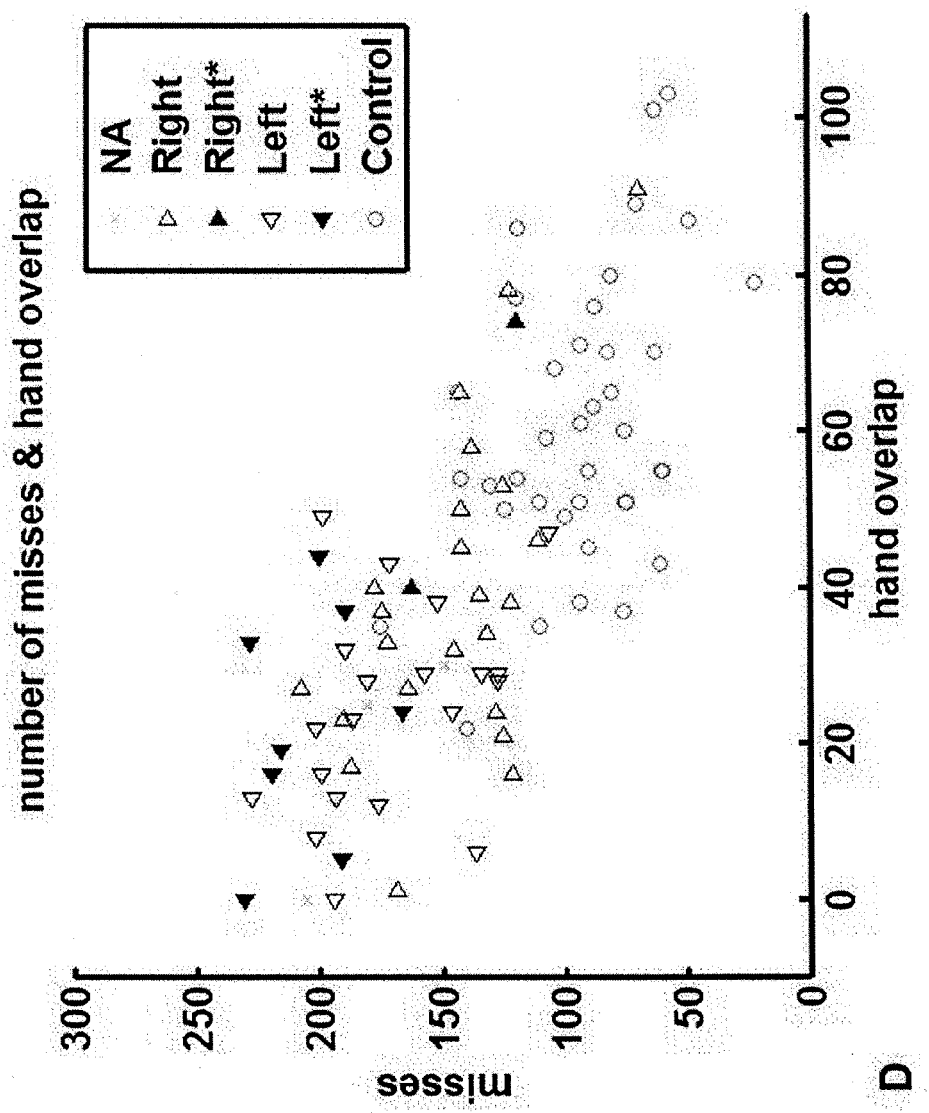
FIG. 2D is a plot showing number of misses and hand overlap for subjects performing an object hitting task as described herein.

FIG. 2D shows the number of misses and hand overlap. There was a large range of values for the overlap among the control group. However, the parameter values were much lower among the stroke participants. The difference between the values was especially profound between the controls and the left-affected subjects, such that 94% of their performance was abnormal (Table 2). This indicates that stroke participants not only made fewer hits, but they did not overlap hands as often as control participants, especially the left-affected stroke group.

Assessing Neurological Impairments

The developed parameters were compared to a clinical Functional Independence Measure (FIM) scores collected for the stroke subjects. Table 2 shows the results of the Spearman correlation between all parameters and the three FIM categories scores (motor, cognitive, total) and the BIT scores.

EXAMPLE 3

Evaluation of Effect of Age

Figure 3A:
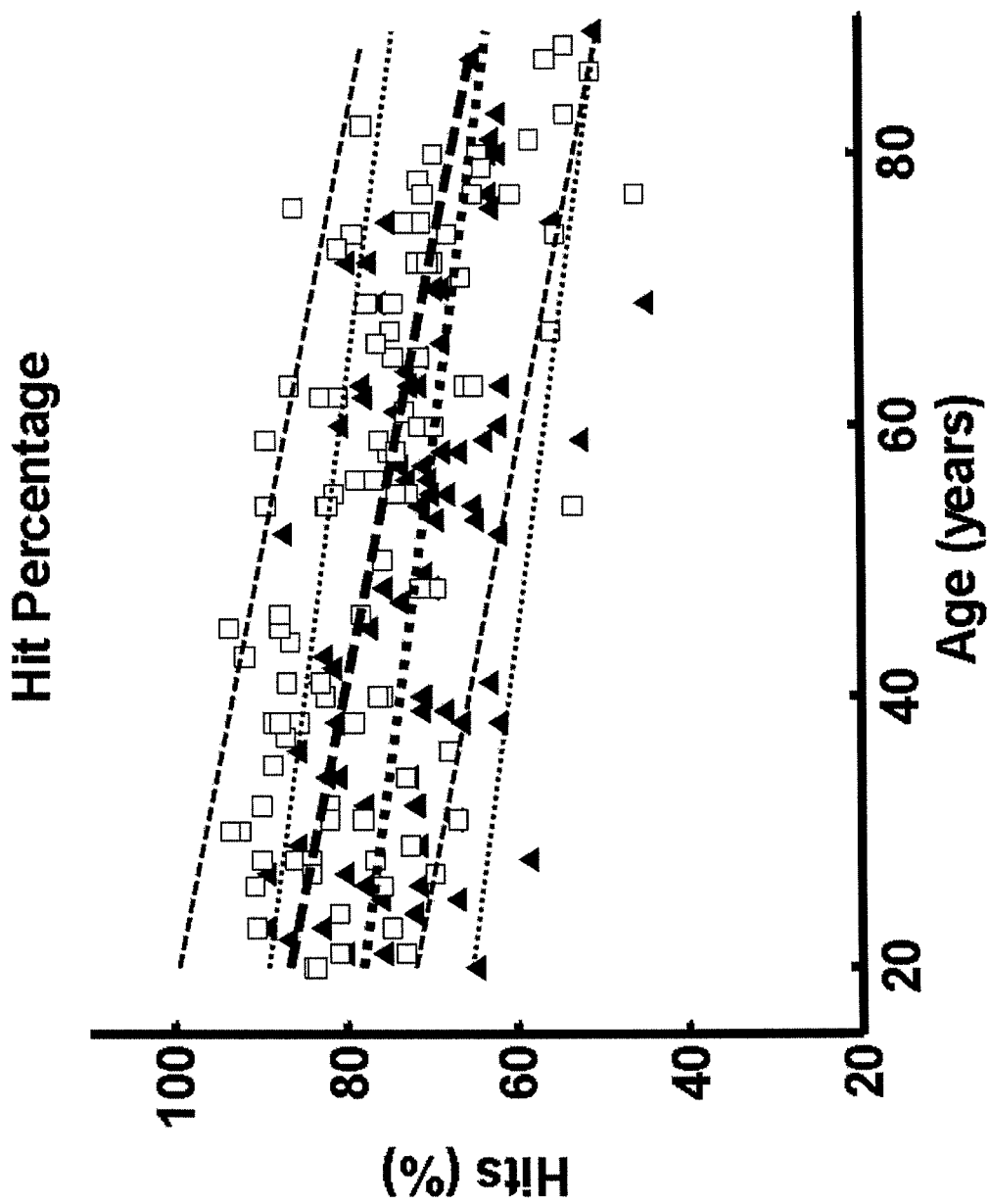
FIGS. 3A-D are plots showing hit percentage (A), miss bias (B), spatial bias (C), and median error (D) as a function of age for an object hitting task. Triangles are female subjects, squares are male subjects.
Figure 3B:
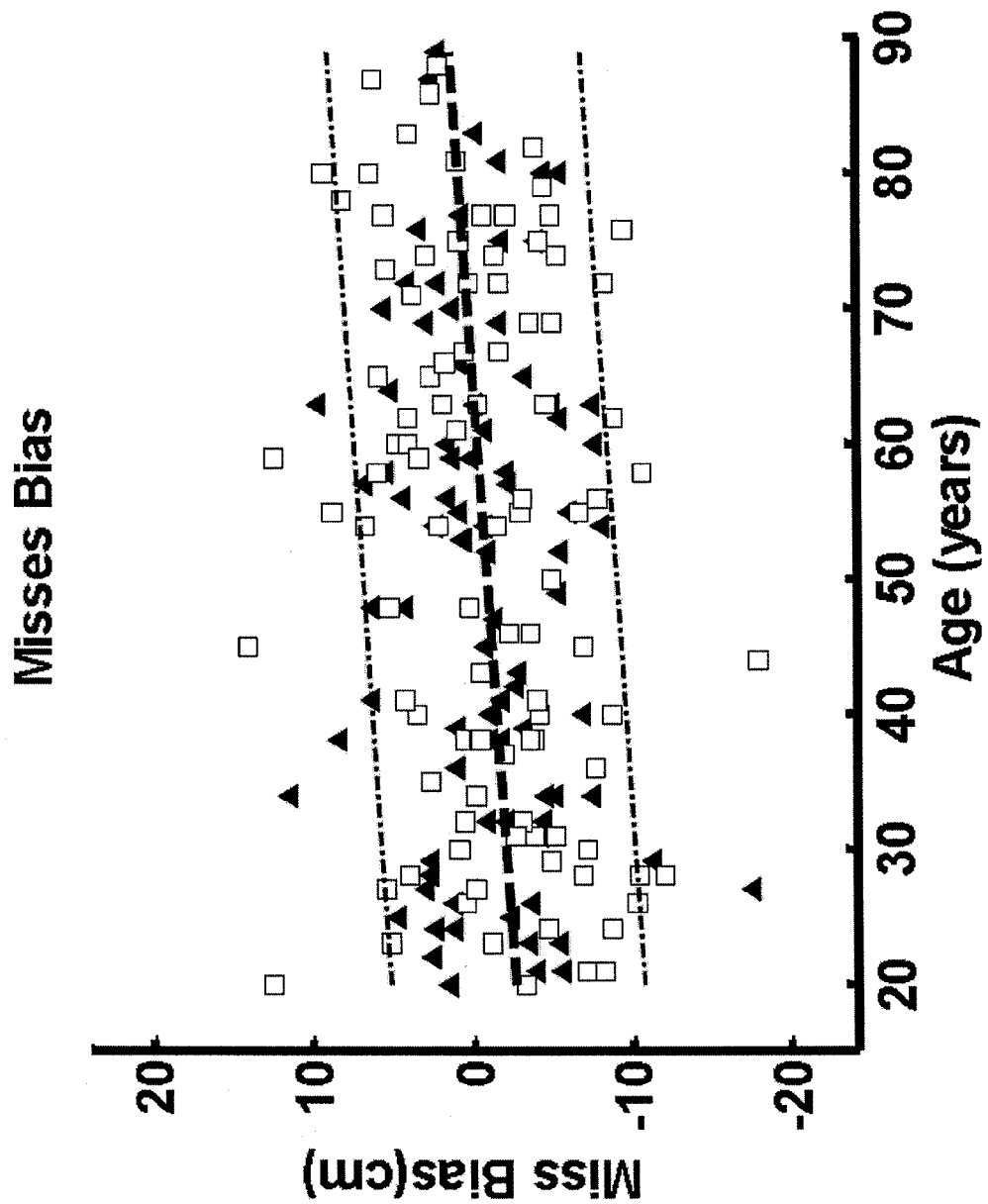
Figure 3C:
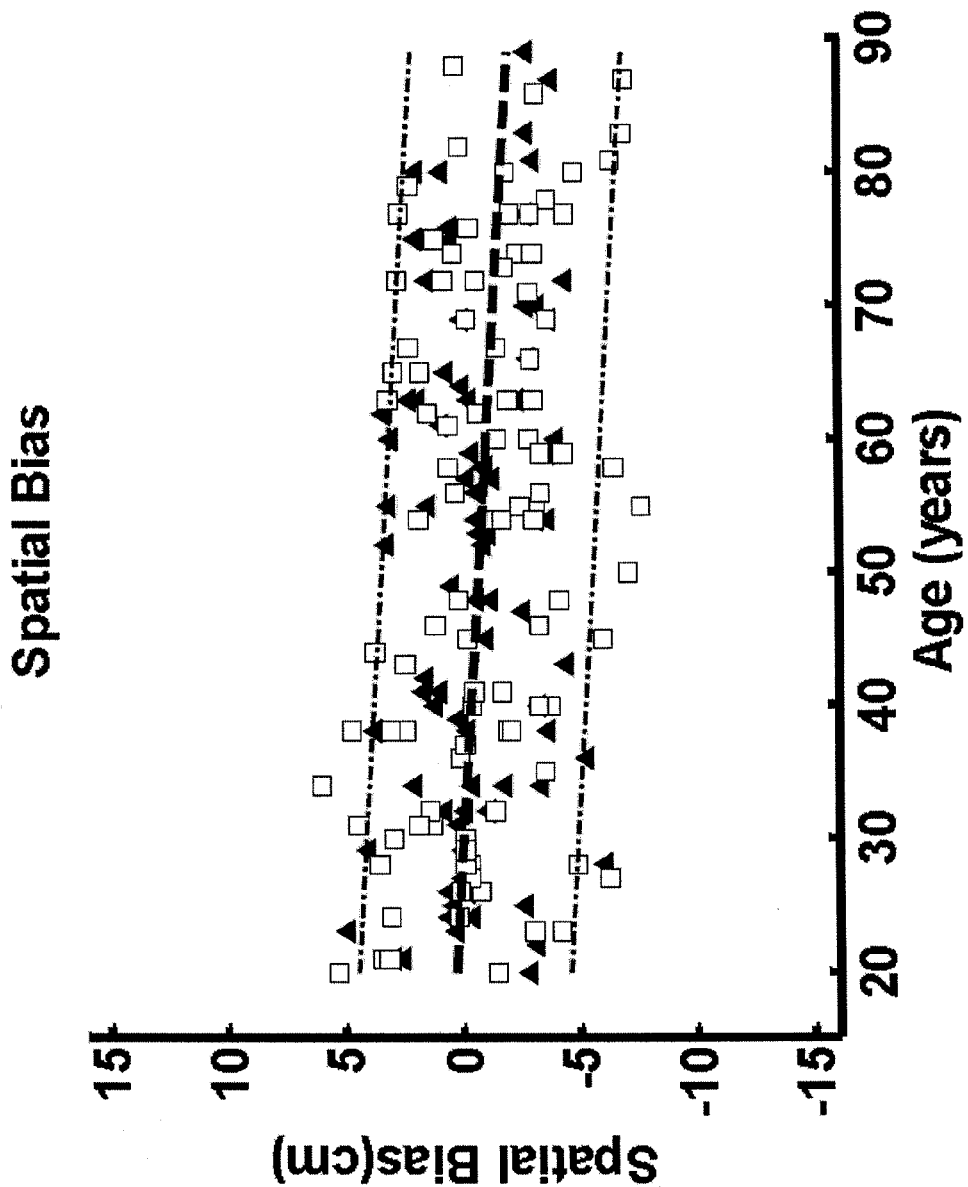
Figure 3D:
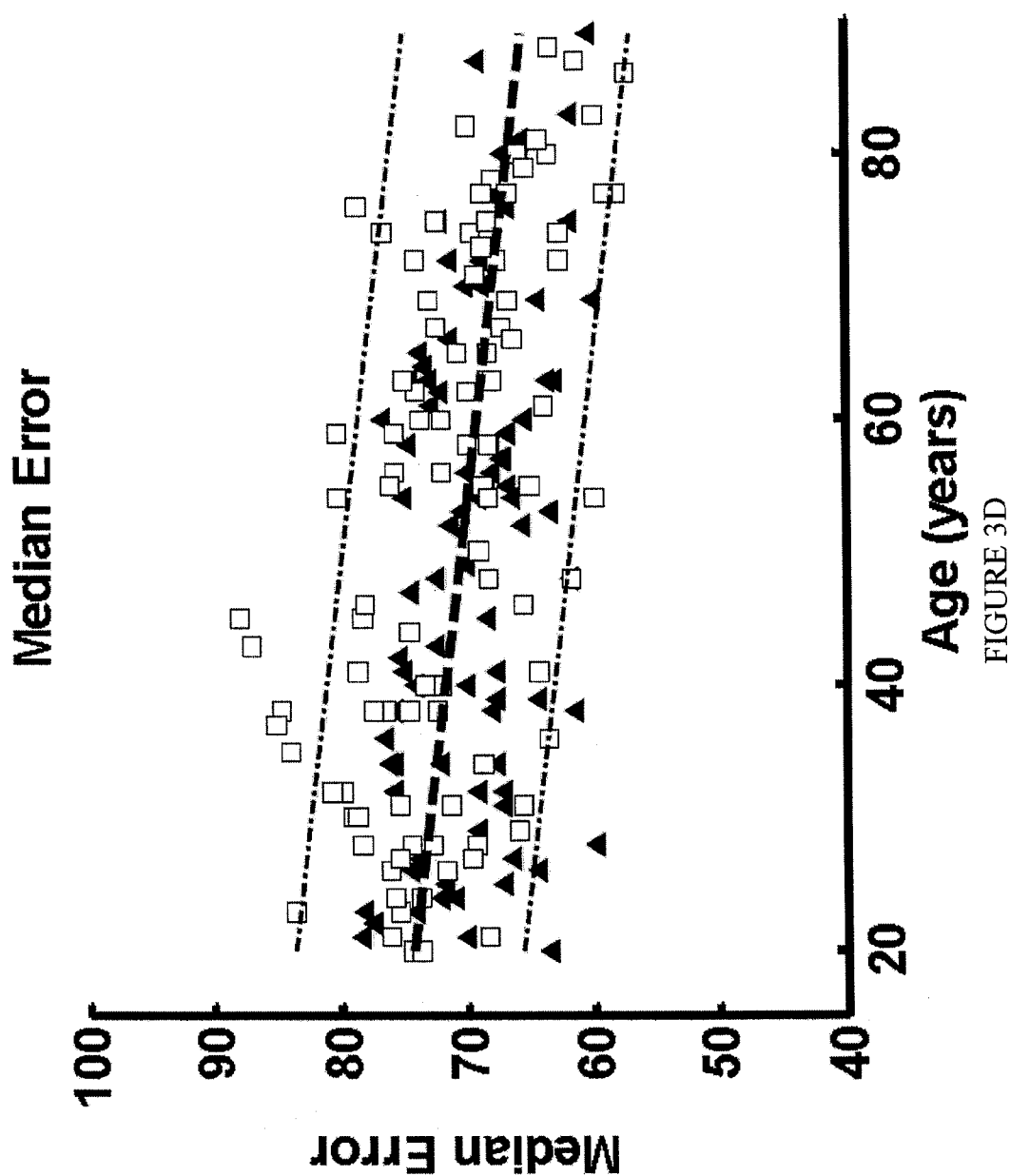

The effects of age, gender, and handedness was examined in our cohort of control subjects. Hand speeds were filtered using sixth order double pass Butterworth low pass filter with cut-off frequency of 10 Hz. Initially, the values for the miss bias, spatial bias, hand bias, total hand area, total hand area bias, hand speed and hand speed bias were flipped for left handed subjects. Subsequently, each parameter was tested for normality and parameters that were identified as not normally distributed (Lilliefor's composite goodness-of-fit, $p<0.01$) were transformed using a log transform (hand selection overlap and hand speed of the non-dominant hand). Then, for each parameter a non-least-squares linear regression was done to identify age-dependent parameters and to identify if there was a difference between males and females (Kolmogorov-Smirnov goodness-of-fit hypothesis test, $p<0.01$). If there were no differences, data from each gender or limb were combined; otherwise data were studied separately (hit percentage and total hand area dominant hand). The separated data was re-tested for normality and age effect. The regression analysis identified two parameters that are gender-affected: hit percentage and total hand area of dominant hand; and four age-affected parameters: hit percentage (males and females) (FIG. 3A), miss bias (FIG. 3B), spatial bias (FIG. 3C), and median error (FIG. 3D).

EXAMPLE 4

Evaluation of Traumatic Brain Injury (TBI) Subjects

Figure 4:
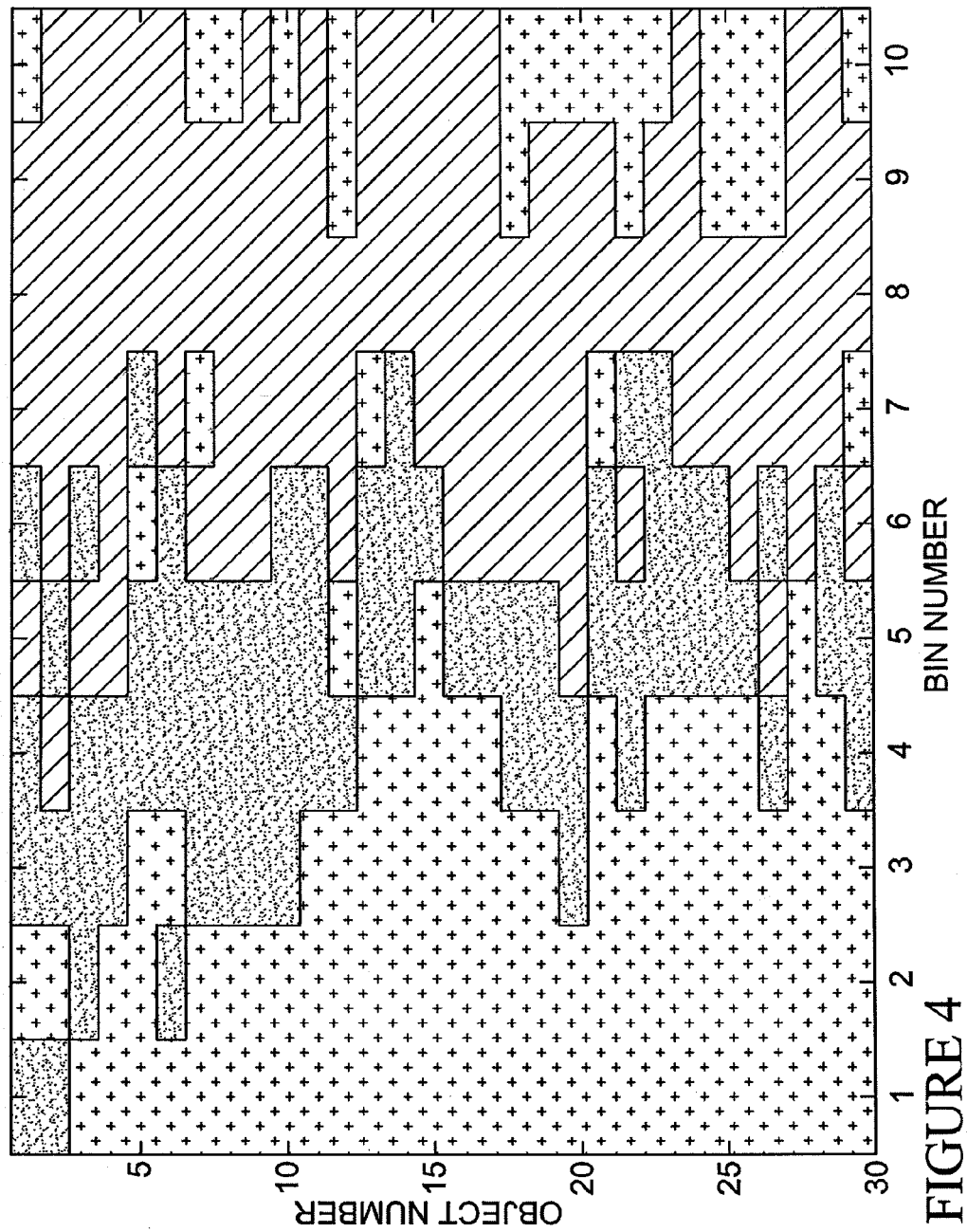
FIG. 4 shows a performance grid for a subject with traumatic brain injury (TBI) in an object hitting task. The format is the same as in FIG. 1D, except successful hits made with the right hand are in diagonal lines, hits with the left hand are stippled, and misses are shown in crosses.

A cohort of 12 subjects with traumatic brain injury (nine severe, two moderate, one mild, based on the Glasgow Coma Scale) were assessed using the object hitting task. Data for one subject is shown in FIG. 4. This subject's TBI history included loss of consciousness for several minutes due to the injury and was a "9" on the Glasgow Coma Scale when first assessed clinically with both a focal and diffuse axonal injury.

The subject was assessed with the object hitting task, as described above, 23 days after the injury and at this point had normal Fugl-Meyer scores for each limb (66), and normal cognitive function based on the MOCA (>27). In the object hitting task, the subject displayed several atypical patterns of behaviour, including many missed objects and these misses are asymmetric with a greater number on the left side of the work space as well as a preference for using the right hand as compared to the left hand for hitting the objects (see FIG. 4).

EXAMPLE 5

Object Hit and Avoid Task with Stroke Subjects

Described herein is an object hit and avoid task, which requires a subject to hit certain target objects (e.g., vertical rectangle and circle) and not hit other distracter objects (e.g., squares and triangles) using either limb of a pair of limbs, such as the arms. As in Example 1, virtual paddles are displayed at the position of the subject's hands and the number and speed of objects presented to the subject increases with time during the task. Target objects can be hit with the paddles including haptic feedback of contact force, whereas distracter objects simply pass through the paddles to remind subjects that these are errors. In total there were 200 target objects to hit and 100 distracters objects not to hit. A large cohort of control subjects (154) was examined to quantify healthy performance, and regressions were performed to quantify age effects on performance.

A cohort of 12 stroke subjects was also assessed with this task. FIG. 5A shows the number of hits that subjects made with the target objects. Eight of the 12 stroke subjects were lower than healthy control subjects. FIG. 5B shows the number of hits that subjects made with the distracter objects. Seven of the 12 stroke subjects hit more distracter targets as compared to control subjects. Ten of the 12 stroke subjects either hit fewer target objects and/or more distracter objects. FIG. 5C shows the movement area bias for stroke and control subjects. Many of the stroke subjects show larger biases than control subjects. Notably, three of the four left-affected subjects (triangles pointing left) had positive biases larger than controls, denoting that the area of space used by their right arm was much larger than the area used by their left arm. In contrast, all six right-affected stroke subjects (triangles pointing right) had movement area biases that were more negative than controls. Thus, this parameter quantifies how performance was biased, with less use of the affected limb as compared to non-affected limb.

EXAMPLE 6

Comparison of Object Hit Task with Object Hit and Avoid Task

Comparison of performance across tasks provides another useful measure of brain function. FIG. 6A shows the number of hits for the object hit task versus the number of hits of target objects in the object hit and avoid task for 12 stroke subjects. The data has been normalized to the $95^{th}$, median, and $5^{th}$ percentiles for age-matched controls. Values above the median are normalized by the difference between the median and $95^{th}$ percentile, whereas values below the median are normalized by the difference between the median and the $5^{th}$ percentile. The figure shows that eight stroke subjects were different from controls in both tasks, and one subject was different from controls only for the object hit task. In general, stroke subject performance tended to be worse for both tasks as compared to controls ($r=0.89$).

A more complex pattern of deficits was observable when quantifying other aspects of performance. FIG. 6B quantifies the relative scores for the movement area bias for the object hit task and the object hit and avoid task. Ten of the 12 stroke subjects exhibit differences from control subjects on one or both tasks: seven stroke subjects were different from controls for the object hit task, whereas nine stroke subjects were different from control subjects in the object hit and avoid task. Although the correlation was high for performance across the two tasks ($r=0.94$), only six subjects failed both tasks. One subject had a significant positive bias for the object hit task which requires hitting a total of 300 targets, but was well within the normal range for the object hit and avoid task, whereas three other subjects displayed the reverse pattern.

These differences are important. For some subjects, the object hitting task emphasizes speed as 300 targets must be hit in a given time period, whereas only 200 targets must be hit for the object hit and avoid task (and avoid the 100 distracter targets). Thus, the increased motor difficulty is associated with poorer performance with regards to symmetry of limb movements for the one subject. In contrast, deficits in limb symmetry were only observed for the object hit and avoid task in three subjects. In this case, limb motor symmetry became worse due to the addition of a cognitive load. Therefore, the engagement of an additional sensory, motor, and/or cognitive function can reveal an impairment in another sensory, motor, and/or cognitive function.

EXAMPLE 7

Object Hit and Avoid Task with Traumatic Brain Injury Subjects

Described herein is the use of an object hit and avoid task (as in Example 5) to quantify brain dysfunction in subjects with traumatic brain injuries. A cohort of eight subjects was tested in this task. FIGS. 7A and 7B show hits for target objects (7A) and distracter objects (7B). Five of the eight subjects hit fewer target objects and/or more distracter objects than healthy controls. In one case, a subject hit many more (43) distracter targets than did healthy controls, but was within the normal range for hitting target objects. The subject understood the instructions as the percentage of hit objects was higher than distracters (~75% of targets and ~40% of distracters). However, the subject clearly had difficulty avoiding the distracters. Three other subjects (all <25 years of age) displayed the opposite pattern with no difficulties missing the distracters but reduced hits of target objects.

EQUIVALENTS

Those skilled in the art will recognize or be able to ascertain variants of the embodiments described herein. Such variants are within the scope of the invention and are covered by the appended claims.

REFERENCES

Coderre, A. M., Abou Zeid, A., Dukelow, S. P., Demmer, M. J., Moore, K. D., Demers, M. J., H., Herter, T. M., Glasgow, J. I., Norman, K. E., Bagg, S. D. and Scott, S. H. (2010) Assessment of upper-limb sensorimotor function of subacute stroke subjects using visually-guided reaching. *Neurorehabiliation and Neural Repair* 24:528-541.

Dukelow, S. P., Herter, T. M., Moore, K. D., Demers, M. J., Glasgow, J. I., Bagg, S. D., Norman, K. E., Scott, S. H. (2010) Quantitative Assessment of Limb Position Sense Following Stroke. *Neurorehabiliation and Neural Repair* 24:178-187.

Kandell, E. R., Schwartz, J. H., Jessell, T. M. (2000) Principles of Neural Science, $4^{th}$ ed. McGraw-Hill, New York.

Teasell, R., Bayona, N., Heitzner, J. (2003) Clinical consequences of stroke. In: Teasell, R. et al., *Stroke Rehabilitation Evidence-Based Review*, 6th edition [monograph on the Internet]. London, ON: Heart & Stroke Foundation of Ontario and Canadian Stroke Network.

Van Deusen, J., Brunt, D. (1997) *Assessment in Occupational Therapy and Physical Therapy*. Philadelphia: W.B. Saunders Co.

The invention claimed is:

1. A method for diagnosing, assessing, or detecting brain injury and/or a neurological disorder of a subject, comprising:
    presenting objects to the subject within the subject's workspace such that the subject can choose to interact with the presented objects using either the right or left limb, or portion thereof, of a pair of limbs;
    using data acquisition apparatus to obtain position data and/or motion data and/or kinetic data of the left and right limbs or portions thereof with respect to a presented object;
    constructing a data set from the obtained data for a plurality of presented objects; and
    analyzing the data set and outputting a result that provides information about condition of the brain and/or neurological status in the subject;
    wherein analyzing comprises determining from the position data and/or motion data and/or kinetic data whether the left limb or right limb was used with respect to a presented object, and repeating the determining for a plurality of presented objects to produce the acquired data set;
    wherein presenting objects includes presenting objects to the subject within the subject's workspace such that two or more objects are in the subject's workspace simultaneously; or
    wherein a next object is presented to the subject before the subject can move the right or left limb, or portion thereof, to a selected position after interacting with a previous object.

2. The method of claim 1, wherein determining includes:
    relating location of a presented object within the subject's workspace to the location of the left limb or right limb that was used to interact with the presented object; and
    repeating the relating for a plurality of presented objects to produce the acquired data set.

3. The method of claim 1, further comprising:
    recording one or more autonomic functions of the subject with respect to a presented object; and
    repeating the recording for a plurality of presented objects;
    wherein data for the one or more autonomic functions together with the acquired data set provide information about brain injury and/or neurological disorder in the subject.

4. The method of claim 3, wherein the one or more autonomic functions are selected from heart rate and blood pressure.

5. The method of claim 1, further comprising:
    presenting the objects to the subject using virtual reality or augmented reality;
    whereby the virtual reality or augmented reality is two-dimensional or three-dimensional.

6. The method of claim 1, wherein:
    the data acquisition apparatus comprises a mechanical linkage;
    wherein the subject's left and right limbs or portions thereof are in contact with the mechanical linkage.

7. The method of claim 6, wherein the mechanical linkage is adapted to be held with the left and right limbs or portions thereof.

8. The method of claim 6, wherein the mechanical linkage is adapted to be attached to left and right limbs or portions thereof.

9. The method of claim 1, wherein:
    the data acquisition apparatus comprises wired or wireless sensors adapted to be attached to left and right limbs of a pair of limbs of a subject, and a detector that detects output signals from the one or more sensors or one or more cameras, to obtain position data and/or motion data and/or kinetic data of the left and right limbs or portions thereof with respect to a presented object.

10. The method of claim 1, further comprising:
    obtaining kinetic trajectory data of a limb with respect to a presented object;
    wherein kinetic trajectory data provide information about brain injury and/or a neurological disorder in the subject.

11. The method of claim 1, further comprising:
    obtaining speed and/or velocity data of a limb with respect to a presented object;
    wherein the speed and/or velocity data provide information about brain injury and/or a neurological disorder in the subject.

12. The method of claim 1, wherein the presented objects include at least one characteristic selected from:
    (i) presented objects are stationary;
    (ii) presented objects are moving;
    (iii) presented objects are moving at different speeds;
    (iv) a fixed number of presented objects at any given time;
    (v) a variable number of presented objects at any given time;
    (vi) presented objects have the same characteristics;
    (vii) presented objects have different characteristics;
    (viii) duration of visibility of each presented object is the same;
    (ix) duration of visibility of each presented object is different;
    wherein data indicating an effect or no effect of a characteristic of a presented object on the subject's behaviour with respect to a presented object provide information about brain injury and/or a neurological disorder in the subject.

13. The method of claim 1, further comprising:
    changing one or more characteristics of the environment in which objects are presented to the subject, including:
    (i) presenting distracter objects, which the subject is instructed not to interact with;
    (ii) presenting barriers, real or virtual, that the subject must move around while attempting to interact or not interact with the objects;
    (iii) presenting workspace-defined force-fields, such as gravity wells;

(iv) presenting audio to the subject;
wherein data indicating an effect or no effect of a characteristic of the environment on the subject's behaviour with respect to a presented object provide information about brain injury and/or a neurological disorder in the subject.

14. The method of claim 1, further comprising:
changing one or more characteristics of the subject's interface in the environment, the one or more characteristics selected from:
(i) providing body-defined force-fields, as a resistance, force, or bias to the subject's limbs;
(ii) modulating spatial and/or temporal alignment of the presented objects relative to the subject's limb movement;
(iii) modulating at least one property of a representation of the subject's limbs used to hit or interact with the objects in the environment, wherein the modulated property is selected from width, length, shape, and a combination thereof; and
(iv) providing a representation of the subject's limb geometry.

15. The method of claim 1, further comprising:
obtaining gaze position data as the subject interacts with the objects;
wherein gaze position data together with the acquired data set provide information about brain injury and/or a neurological disorder in the subject.

16. The method of claim 1, wherein analyzing comprises comparing the data set with control data.

17. Apparatus for diagnosing, assessing, or detecting brain injury and/or a neurological disorder of a subject, comprising:
a display device that presents objects to the subject within the subject's workspace such that the subject can choose to interact with the presented objects using either the right or left limb, or portion thereof, of a pair of limbs, wherein the display device displays a representation of the subject's limbs or portions thereof;
data acquisition apparatus that obtains position data and/or motion data and/or kinetic data of the left and right limbs or portions thereof with respect to a presented object; and
computer readable media that directs a computer to perform one or more of:
present the objects on the display device such two or more objects are in the subject's workspace simultaneously; or such that a next object is presented to the subject before the subject can move the right or left limb, or portion thereof, to a selected position after interacting with a previous object;
present the representation of the subjects limbs or portions thereof on the display device;
input and analyze the position data and/or motion data and/or kinetic data corresponding to the subject's left limb and right limb with respect to the presented objects; including determining from the position data and/or motion data and/or kinetic data whether the left limb or right limb was used with respect to a presented object, and repeating the determining for a plurality of presented objects;
output information about condition of the brain and/or neurological status in the subject.

18. The apparatus of claim 17, wherein the data acquisition apparatus that obtains position data and/or motion data and/or kinetic data of the limbs comprises a mechanical linkage adapted to be attached to each limb.

19. The apparatus of claim 17, wherein the data acquisition apparatus that obtains position data and/or motion data and/or kinetic data of the limbs comprises a mechanical linkage adapted to be grasped by the subject.

20. The apparatus of claim 17, wherein the data acquisition apparatus that obtains position data and/or motion data and/or kinetic data of the limbs comprises one or more sensors adapted to be attached to each limb, and a detector that detects output signals from the one or more sensors, or one or more cameras.

21. A method for obtaining position data and/or motion data and/or kinetic data of the left and right limbs or portions thereof of a subject, comprising:
presenting objects to the subject within the subject's workspace such that the subject can choose to interact with the presented objects using either the right or left limb, or portion thereof, of a pair of limbs;
using data acquisition apparatus to obtain position data and/or motion data and/or kinetic data of the left and right limbs or portions thereof with respect to a presented object;
constructing a data set from the obtained data for a plurality of presented objects; and
analyzing the data set and outputting a result that provides information about condition of the brain and/or neurological status in the subject;
wherein analyzing comprises determining from the position data and/or motion data and/or kinetic data whether the left limb or right limb was used with respect to a presented object, and repeating the determining for a plurality of presented objects to produce the acquired data set;
wherein presenting objects includes presenting objects to the subject within the subject's workspace such that two or more objects are in the subject's workspace simultaneously; or
wherein a next object is presented to the subject before the subject can move the right or left limb, or portion thereof, to a selected position after interacting with a previous object.

22. The method of claim 21, further comprising using the result to diagnose, assess, or detect brain injury and/or a neurological disorder in the subject.

23. A method of diagnosing, assessing, or detecting brain injury and/or a neurological disorder of a subject, comprising:
analyzing a data set to determine a brain injury and/or a neurological disorder of a subject;
wherein the data set is obtained by:
presenting objects to the subject within the subject's workspace such that the subject can choose to interact with the presented objects using either the right or left limb, or portion thereof, of a pair of limbs;
using data acquisition apparatus to obtain position data and/or motion data and/or kinetic data of the left and right limbs or portions thereof with respect to a presented object;
constructing the data set from the obtained data for a plurality of presented objects;
wherein presenting objects includes presenting objects to the subject within the subject's workspace such that two or more objects are in the subject's workspace simultaneously; or
wherein a next object is presented to the subject before the subject can move the right or left limb, or portion thereof, to a selected position after interacting with a previous object;

or wherein the data set is obtained by:

presenting objects to the subject within the subject's workspace such that the subject can choose to interact with the presented objects using either the right or left limb, or portion thereof, of a pair of limbs;

presenting one or more distractions to the subject while the subject is interacting with a presented object;

using data acquisition apparatus to obtain position data and/or motion data and/or kinetic data of the left and right limbs or portions thereof with respect to a presented object; and constructing the data set by obtaining position data and/or motion data and/or kinetic data of the left and right limbs or portions thereof for a plurality of presented objects;

wherein analyzing comprises determining from the position data and/or motion data and/or kinetic data whether the left limb or right limb was used with respect to a presented object, and repeating the determining for a plurality of presented objects; and outputting a result that provides information about condition of the brain and/or neurological status in the subject.

* * * * *